United States Patent
Mecozzi et al.

(10) Patent No.: US 10,426,727 B2
(45) Date of Patent: Oct. 1, 2019

(54) FLUOROPOLYMER EMULSIONS WITH BRANCHED SEMIFLUORINATED BLOCK COPOLYMER OR PHOSPHOLIPID SURFACTANT FOR THE DELIVERY OF HYDROPHOBIC DRUGS

(71) Applicant: Wisconsin Alumni Research Foundation, Madison, WI (US)

(72) Inventors: Sandro Mecozzi, Madison, WI (US); Robert A. Pearce, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 9 days.

(21) Appl. No.: 15/306,714

(22) PCT Filed: Apr. 24, 2015

(86) PCT No.: PCT/US2015/027577
§ 371 (c)(1),
(2) Date: Oct. 25, 2016

(87) PCT Pub. No.: WO2015/164781
PCT Pub. Date: Oct. 29, 2015

(65) Prior Publication Data
US 2017/0049699 A1    Feb. 23, 2017

Related U.S. Application Data

(60) Provisional application No. 61/984,653, filed on Apr. 25, 2014.

(51) Int. Cl.
*A61K 9/107* (2006.01)
*A61K 9/00* (2006.01)
(Continued)

(52) U.S. Cl.
CPC .......... *A61K 9/1075* (2013.01); *A61K 9/0019* (2013.01); *A61K 31/05* (2013.01);
(Continued)

(58) Field of Classification Search
CPC ... C08L 2203/02; C08L 71/02; C08G 65/337; C08G 81/00
See application file for complete search history.

(56) References Cited

U.S. PATENT DOCUMENTS 3,989,843 A    11/1976    Chabert et al.
6,113,919 A    9/2000    Reiss et al.
(Continued)

FOREIGN PATENT DOCUMENTS

EP    0391637 A1    10/1990
WO    WO 2005/067517 A2    7/2005
(Continued)

OTHER PUBLICATIONS

Adam, et al., "Pharmacokinetics in laboratory animals of ICI 35 868, a new i.v. anaesthetic agent", *Br. J. Anaesth.*, 52:743-746 (1980).
(Continued)

*Primary Examiner* — Kortney L. Klinkel
(74) *Attorney, Agent, or Firm* — Leydig, Voit & Mayer, Ltd.

(57) ABSTRACT

The present invention provides therapeutic formulations, including therapeutic nanoemulsions, and related methods for the in vivo delivery of hydrophobic compounds, including an important class of hydrophobic anesthetics. Formulations and methods of the invention include semifluorinated block copolymers, and optionally phospholipid surfactants, capable of forming a stable nanoemulsion without the need of conventional lipid components that support bacterial and/or fungal growth (e.g., soybean oil and similar lipids). In
(Continued)

certain embodiments, emulsion-based formulations are provided that are capable of formulating, delivering and releasing amounts of hydrophobic drugs effective for a range of clinical applications, including inducing and maintaining anesthesia in patients. In certain embodiments, emulsion-based formulations are provided that are capable of supporting controlled release, for example, over a range of rates useful for clinical applications including rapid and sustained release.

25 Claims, 12 Drawing Sheets

(51) Int. Cl.
  A61K 47/24 (2006.01)
  A61K 47/34 (2017.01)
  A61K 31/05 (2006.01)
  A61K 31/57 (2006.01)
  A61K 47/10 (2017.01)
  A61K 47/46 (2006.01)
  C08G 65/337 (2006.01)
  C08G 81/00 (2006.01)
  C08L 71/02 (2006.01)

(52) U.S. Cl.
  CPC .............. A61K 31/57 (2013.01); A61K 47/10 (2013.01); A61K 47/24 (2013.01); A61K 47/34 (2013.01); A61K 47/46 (2013.01); C08G 65/337 (2013.01); C08G 81/00 (2013.01); C08L 71/02 (2013.01); C08L 2203/02 (2013.01)

(56) References Cited

U.S. PATENT DOCUMENTS

| | | |
|---|---|---|
| 8,900,562 B2 | 12/2014 | Mecozzi et al. |
| 9,000,048 B2 | 4/2015 | Mecozzi et al. |
| 2004/0057906 A1 | 3/2004 | Hsu et al. |
| 2017/0100336 A1 | 4/2017 | Mecozzi et al. |

FOREIGN PATENT DOCUMENTS

| | | |
|---|---|---|
| WO | WO 2008/070490 A2 | 6/2008 |
| WO | 2015/164756 | 10/2015 |
| WO | 2018/187236 | 10/2018 |

OTHER PUBLICATIONS

Babu, et al., "Toward the development of an injectable dosage form of propofol: preparation and evaluation of propofol-sulfobutyl ether 7-beta-cyclodextrin complex", *Pharm. Dev. Technol.*, 9: 265-275 (2004).
Baker, et al., "Propofol—The Challenges of Formulation", *Anesthesiology, American Society of Anesthesiologists*, 103(4): 860-876 (2005).
Bennett et al., "Postoperative infections traced to contamination of an intravenous anesthetic, propofol", *N. Engl. J. Med.*, 333:147-154 (1995).
Brammer, et al., "A comparison of propofol with other injectable anaesthetics in a rat model for measuring cardiovascular parameters", *Lab. Anim.*, 27:250-257 (1993).
Cai et al., "A propofol microemulsion with low free propofol in the aqueous phase: formulation, physicochemical characterization, stability and pharmacokinetics", *Int. J. Pharm.*, 436:536-544 (2012).
Damitz et al., "Rapid dissolution of propofol emulsions under sink conditions", *Int. J. Pharm.*, 481:47-55 (2015).
Damitz et al., "Propofol emulsion-free drug concentration is similar between batches and stable over time", *Romanian Journal of Anaesthesia and Intensive Care*, 23(1): 7-11 (2016).
Damitz, et al., "Kinetically stable propofol emulsions with reduced free drug concentration for intravenous delivery", *Int. J. Pharm.*, 486:232-241 (2015).
De Leon-Casasola et al., "Anaphylaxis due to propofol", *Anesthesiology*, 77:384-386 (1992).
Di Gregorio, et al., "Lipid emulsion in superior to vasopressin in a rodent model of resuscitation from toxin-induced cardiac arrest", *Crit. Care Med.*, 37:993-999 (2009).
Dubey, et al., "Pain on injection of lipid-free propofol and propofol emulsion containing medium-chain triglyceride: A comparative study", *Anesth. Analg.*, 101:1060-1062 (2005).
Egan, et al., "The pharmacokinetics and pharmacodynamics of propofol in a modified cyclodextrin formulation (Captisol) versus propofol in a lipid formulation (Diprivan): an electroencephalographic and hemodynamic study in a porcine model", *Anesth. Analg.*, 97:72-79 (2003).
Fast, et al., "Fluoropolymer-based emulsions for the intravenous delivery of sevoflurane", *Anesthesiology*, 109:651-656 (2008).
Glen, et al., "Pharmacology of an emulsion formulation of ICI 35 868", *Br. J. Anaesth.*, 56:617-626 (1984).
Han et al., "Physical properties and stability of two emulsion formulations of propofol", *Int. J. Pharm.*, 215: 207-220 (2001).
Hansch, et al., "Exploring QSAR—Hydrophobic, Electronic, and Steric Constants", *Washington, DC: American Chemical Society*, p. 159 (1995).
Hiller, et al., "Safety of high volume lipid emulsion infusion a first approximation of LD50 in rats", *Reg. Anesth. Pain Med.*, 35:140-144 (2010).
Jamaty, et al., "Lipid emulsions in the treatment of acute poisoning: a systematic review of human and animal studies", *Clin. Toxicol.* (Phila), 48:1-27 (2010).
Jee et al., "Exceptionally stable fluorous emulsions for the intravenous elivery of volatile general anesthetics", *Anesthesiology*, 116(3): 580-585 (2012).
Jung, et al., "Effectiveness, safety, and pharmacokinetic and pharmacodynamics characteristics of microemulsion propofol in patients undergoing elective surgery under total intravenous anaesthesia", *Br. J. Anaesth.*, 104:563-756 (2010).
Krafft, et al., "Fluorocarbons and fluorinated amphiphiles in drug delivery and biomedical research", *Adv. Drug Deliv. Rev.*, 47:209-228 (2002).
Langevin et al., "Growth of *Staphylococcus aureus* in Diprivan and Intralipid: Implications on the pathogenesis of infections", *Anesthesiology*, 91:1394-1400 (1999).
Laxenaire, et al., "Anaphylactic shock due to propofol", *Lancet*, 2:739-740 (1988).
Lee et al., "Physicochemical properties, pharmacokinetics and pharmacodynamics of a reformulated microemulsion propofol in rats", *Anesthesiology*, 109:436-447 (2008).
Liao et al., "R (+) etomidate and the photoactivable R (+) azietomidate have comparable anesthetic activity in wild-type mice and comparably decreased activity in mice with a N265M point mutation in the gamma-aminobutyric acid receptor B3 subunit", *Anesth. Analg.*, 101:131-135 (2005).
Mayette, et al., "Propofol infusion syndrome resuscitation with extracorporeal life support: a case report and review of the literature",*Ann. Intensive Care*, 3:32 (2013).
Ohmizo, et al., "Mechanism of injection pain with long and long-medium chain triglyceride emulsive propofol", *Can. J. Anaesth.*, 52: 595-599 (2005).
Park et al., "The effect if lidocaine on the globule size distribution of propofol emulsions", *Anesth. Analg.*, 97:769-771 (2003).
Perez, et al., "Determining the optimal dose of intravenous fat emulsion for the treatment of severe verapamil toxicity in a rodent model", *Acad. Emerg. Med.*, 15:1284-1289 (2008).
Pergolizzi, et al., "Perspectives on the role of fospropofol in the monitored anesthesia care setting", *Anesthesiol. Res. Pract.*, 458920 (2011).
Rau, et al., "Propofol in an emulsion of long- and medium chain triglycerides: the effect on pain", *Anesth. Analg.*, 93:382-384 (2001).

(56) References Cited

OTHER PUBLICATIONS

Riess, "Oxygen carriers ("blood substitutes")-raison d'etre, chemistry, and some physiology", *Chem Rev.*, 101:2797-2920 (2001).

Riess, et al., "Highly fluorinated systems for oxygen transport, diagnosis and drug delivery", *Colloids and Surfaces A: Physiochemical and Engineering Aspects*, 84(1): 33-48 (1994).

Rosen et al., "Too much of a good thing? Tracing the history of the propofol infusion syndrome", *J. Trauma*, 63:443-447 (2007).

Schmutz et al., "Fluorinated Vesicles Made from Combinations of Phospholipids and Semifluorinated Alkanes. Direct Experimental Evidence of the Location of the Semifluorinated Alkane within the Bilayer", *Langmuir*, 19:4889-4894 (2003).

Sim, et al., "Pain on injection with microemulsion propofol", *Br. J. Clin. Pharmacol.*, 67: 316-325 (2009).

Song et al.,"The pharmacodynamic effects of a lower-lipid emulsion of propofol: a comparison with the standard propofolemulsion", *Anesth. Analg.*, 98:687-691 (2004).

Tan, et al., "Pain on injection of propofol", *Anesthesia*, 53:468-476 (1998).

Thompson, et al., "The recent development of propofol (DIPRIVAN)", *Intens. Care Med.*, 26 (Suppl. 4): S400L 404 (2000).

Tucker, et al., "Synthesis, physicochemical characterization, and self-assembly of linear, dibranched and miktoarm semifluorinated triphilic polymers", *J. Polym. Sci. A: Polym. Chem.*, 52:3324-3336 (2014).

Wachowski, et al., "The growth of microorganisms in propofol and mixtures of propofol and lidocaine", *Anesth. Analg.*, 88:209-212 (1999).

Weinberg, et al., "Pretreatment or resuscitation with a lipid infusion shifts the dose-response to bupivacaine-induced asystole in rats", *Anesthesiology*, 88:1071-1075 (1998).

Weinberg, "Lipid emulsion infusion resuscitation for local anesthetic and other drug overdose", *Anesthesiology*, 117:180-187 (2012).

Weinberg et al., "Lipid emulsion infusion rescues dogs from bupivacaine-induced cardiac toxicity", *Reg. Anesth. Pain Med.*, 38:198-202 (2003).

Wolf et al., "Impaired fatty acid oxidation in propofol infusion syndrome", *Lancet*, 357:606-607 (2001).

Wong, "Propofol infusion syndrome", *Am. J. Ther.*, 17:487-491 (2010).

European Patent Office, International Search Report in International Application No. PCT/US2015/027577 (dated Sep. 28, 2015).

FLUOROPOLYMER EMULSIONS WITH BRANCHED SEMIFLUORINATED BLOCK COPOLYMER OR PHOSPHOLIPID SURFACTANT FOR THE DELIVERY OF HYDROPHOBIC DRUGS

CROSS-REFERENCE TO RELATED APPLICATIONS

This application is a U.S. National Stage Application filed under 35 U.S.C. § 371 of International Application No. PCT/US2015/027577, filed Apr. 24, 2015, which claims the benefit of U.S. Provisional Application No. 61/984,653, filed Apr. 25, 2014. All of these applications are hereby incorporated by reference in their entireties.

STATEMENT REGARDING FEDERALLY SPONSORED RESEARCH OR DEVELOPMENT

Not applicable.

BACKGROUND

Administration of hydrophobic drugs presents practical challenges due to the limited water solubility of this class of pharmaceuticals. Accordingly, a primary focus of drug delivery research is development of effective approaches for the formulation and controlled delivery for this class of important pharmaceutical agents. Nanoemulsions are a particularly promising delivery vehicle for these applications given their intrinsic stability and potential to access useful pharmacokinetic properties for drug administration, absorption and targeting.

Nanoemulsions are composed of nanoscale droplets of one immiscible liquid dispersed within another. In the context of many pharmaceutical applications, for example, the dispersed droplet phase of a nanoemulsion provides a central oil core, stably dispersed in an aqueous phase, that can act as an effective reservoir for hydrophobic drugs. Nanoemulsions for delivery applications often incorporate one or more surfactants and/or stabilizers to facilitate stabilization and improve drug solubilization of the dispersed phase. As nonequilibrium systems, preparation of a nanoemulsion typically involves an input of energy, for example, using a microfluidiser, high pressure homogeniser or ultrasonicator.

Typical droplet sizes for nanoemulsions for the delivery of pharmaceuticals are in the range of about 20-500 nm. The small droplet size characteristic of nanoemulsions provides benefits supporting their use as vehicles for pharmaceutical delivery. First, the small droplet size and lower surface tension between dispersed and aqueous phases decrease the rates of droplet agglomeration and precipitation processes so as to substantially limit the potential for phase separation via sedimentation, flocculation, coalescence and creaming. As a result, nanoemulsions are typically more kinetically stable than other types of emulsions. Second, the nanosized dimensions of the droplets allow for effective in vivo administration, for example via drug absorption from the gastrointestinal tract or penetration of the skin barrier. Third, the large interfacial area provided by the small size of the dispersed droplets allows for the potential to effectively control drug release over a clinically useful range. Accordingly, nanoemulsions have significant potential for providing rapid, sustained or targeted delivery and release of hydrophobic drugs.

While emulsions have long been used for topical administration, recent research has been directed to development of emulsion-based delivery systems effective for parenteral, inhalation and oral delivery. Phospholipid-stabilized soybean oil emulsions were the first approved intravenous emulsion and have been used clinically as i.v. nutritional supplements for over 40 years. More recently, however, emulsions have been developed and employed widely in the clinic for the delivery of certain hydrophobic drugs, such as anesthetics, anti-inflammatory and analgesic drugs, and also as blood substitutes.

Commercial propofol (i.e., Diprivan), for example, consists of an Intralipid® emulsion of the active agent 2,6-diisopropylphenol. The lipid emulsion-based formulation of propofol is used extensively for anesthesiology practices for inducing and maintaining general anesthesia. In addition, this emulsion-based formulation of propofol is used for procedural sedation and sedation in intensive care settings. Current lipid emulsion-based formulations of propofol are susceptible to problems relating to the ability of their lipid component (e.g. soybean oil) to support bacterial and fungal growth. To address the risk of contamination, for example, tubing and open vials of propofol must be replaced every twelve hours for many clinical applications. In addition, infusion at high rates or as large bolus can result in lipid intolerance, which may contribute to propofol infusion syndrome, a rare but serious complication that further limits use of lipid-based emulsions of propofol in intensive care settings.

It will be appreciated from the foregoing that emulsion-based delivery systems for the formulation and administration of hydrophobic drugs are needed. Systems and formulations are needed that are capable of providing stable formulation of hydrophobic drugs exhibiting sparing solubility in aqueous solutions, particularly, in concentrations supporting a range of important clinical applications. Systems and formulations are needed exhibiting a high degree of biocompatibility, low toxicity and pharmacokinetic properties supporting controlled delivery and targeting of hydrophobic drugs.

SUMMARY OF THE INVENTION

The present invention provides therapeutic formulations, including therapeutic nanoemulsions, and related methods for the in vivo delivery of hydrophobic compounds, including an important class of hydrophobic anesthetics. Formulations and methods of the invention include semifluorinated block copolymers, and optionally phospholipid surfactants, capable of forming a stable nanoemulsion without the need for conventional lipid components that support bacterial and/or fungal growth (e.g., soybean oil and similar lipids). In certain embodiments, emulsion-based formulations are provided that are capable of formulating, delivering and releasing amounts of hydrophobic drugs effective for a range of clinical applications, including inducing and maintaining anesthesia in patients. In certain embodiments, emulsion-based formulations are provided that are capable of supporting controlled release, for example, over a range of rates useful for clinical applications including rapid and sustained release.

In certain embodiments, nanoemulsion formulations of the present invention include linear or branched semifluorinated block copolymers, and optionally phospholipid surfactants, having a composition resulting in enhanced stability with respect to droplet size by decreasing the rate of Ostwald ripening, coagulation and/or phase separation processes. Therapeutic formulations of the present invention also provide a high degree of versatility, as the amount and composition of the semi-fluorinated block copolymer component (e.g., length and composition of the hydrophilic block, length and composition of the fluorophilic block, length and composition of the hydrophobic block, etc.), and optionally the amount and chemical composition of phospholipid surfactant may be selectively adjusted to: (i) enhance stability under delivery conditions, (ii) optimize the kinetics of release of a hydrophobic compound for a specific application (e.g. provide faster or slower release rates), and (iii) enhance the overall formulation stability of therapeutic nanoemulsions under storage conditions (e.g., increase useful shelf life).

In an embodiment, the present formulations comprise linear or branched semi-fluorinated block copolymers having hydrophilic, hydrophobic and fluorophilic blocks, and optionally a stabilizing additive, such as a phospholipid surfactant, capable of generating an emulsion of a clinically effective amount of a hydrophobic compound, such as propofol, dispersed in an aqueous solution. Therapeutic formulations of the present invention include nanoemulsions comprising submicron droplets of a hydrophobic compound dispersed in a continuous phase comprising an aqueous solution, such as an aqueous solution isotonic to blood plasma. In some embodiments, droplets of the hydrophobic compound of the emulsion are stabilized by the formation of supramolecular structures of self-assembled semi-fluorinated block copolymer surfactants that reduce the interfacial tension of the hydrophobic compound at the droplet interface with the continuous aqueous phase. In some embodiments, for example, surfactant comprising linear or branched semi-fluorinated block copolymers having a hydrophilic block, hydrophobic block and a fluorophilic block self-assemble upon emulsification to form supramolecular structures dispersed in an aqueous continuous phase, thereby encapsulating and stabilizing significant quantities of the hydrophobic compound component in a hydrophobic intermediate shell. For example, the hydrophobic block of the semifluorinated block copolymers may form an inner shell or core of the supramolecular structure, thereby functioning as a molecular recognition element for the hydrophobic compound. Optionally, the dispersed phase droplets of hydrophobic compound may also have a stabilizing additive component for providing useful chemical and physical properties. In some embodiments, for example, the nanoemulsions of the invention are useful for formulation and administration of hydrophobic anesthetic agents, such as propofol In an embodiment of this aspect, the emulsion is a nanoemulsion, for example, characterized by a dispersed phase comprising droplets having cross sectional dimensions selected from the range of 20 nm to 1 micron, and optionally selected from the range of 100 nm to 1 micron. In an embodiment, the dispersed phase droplets comprise a hydrophobic therapeutic agent, optionally the semi-fluorinated block copolymers, wherein said droplets have an average diameter less than or equal to 1000 nanometers, preferably for some applications an average diameter less than or equal to 500 nanometers, and more preferably for some applications an average diameter less than or equal to 300 nanometers. Optionally, the therapeutic formulation of this aspect of the present invention is capable of delivery to a patient via parenteral administration, such as via intravenous injection.

In an aspect, the present invention provides emulsion-based formulations, such as nanoemulsions. For example, in one embodiment, an emulsion of the invention is useful for delivery of a therapeutic agent comprising a hydrophobic drug. Emulsions of this aspect are beneficial, for example, for delivering therapeutic agents comprising a hydrophobic compound to a patient or subject, such as a therapeutic agent which is insoluble or only sparingly soluble in aqueous solution. For example, in some embodiments, hydrophobic therapeutic agents which are soluble in aqueous solutions at concentrations or dosages less than a useful therapeutic amount benefit from the emulsions of the invention, which provide for the ability to deliver a therapeutic or effective amount of the therapeutic agent to a patient or subject.

In an aspect, an emulsion of the invention comprises: an aqueous solution, semi-fluorinated block copolymers, a therapeutic agent comprising a hydrophobic compound and a phospholipid surfactant. In embodiments, for example, each of the semi-fluorinated block copolymers independently comprises a hydrophilic block, a hydrophobic block and a fluorophilic block, such as where the hydrophobic block of each of the semi-fluorinated block copolymers is provided between the fluorophilic block and the hydrophilic block; or wherein each of said semi-fluorinated block copolymers has a branched structure wherein said hydrophilic block comprises a first branch, said hydrophobic block comprises a second branch and said fluorophilic block comprises a third branch. In an embodiment, the semi-fluorinated block copolymers comprise linear block copolymers, for example, wherein the hydrophobic block of each of the semi-fluorinated block copolymers is provided between the fluorophilic block and the hydrophilic block. In an embodiment, the semi-fluorinated block copolymers comprise branched block copolymers, for example, wherein said hydrophilic block comprises a first branch, said hydrophobic block comprises a second branch and said fluorophilic block comprises a third branch. The invention includes emulsions comprising more than one type of the semi-fluorinated block copolymer, such as a mixture of linear and branched the semi-fluorinated block copolymers.

In exemplary embodiments, for example, the emulsion comprises a continuous phase and a dispersed phase, such as where the continuous phase comprises the aqueous solution and the dispersed phase comprises the semi-fluorinated block copolymers, the therapeutic agent and the phospholipid surfactant.

In another aspect, an emulsion of the invention comprises: an aqueous solution, semi-fluorinated block copolymers, and a therapeutic agent comprising a hydrophobic compound. In embodiments, for example, each of the semi-fluorinated block copolymers independently comprises a hydrophilic block, a hydrophobic block and a fluorophilic block, such as where each of the semi-fluorinated block copolymers has a branched structure and where the hydrophilic block comprises a first branch, the hydrophobic block comprises a second branch and the fluorophilic block comprises a third branch. In exemplary embodiments, for example, the emulsion comprises a continuous phase and a dispersed phase, such as where the continuous phase comprises the aqueous solution and the dispersed phase comprises the semi-fluorinated block copolymers and the therapeutic agent.

Emulsions of the invention for certain applications optionally exclude certain substances or mixtures of substances from either or both the dispersed phase and the aqueous phase. Emulsions of the invention optionally include certain substances or mixtures in either or both the dispersed phase and the aqueous phase. For example, in some embodiments, certain substances or mixtures are either explicitly excluded from or included in the emulsion in order to control the physical properties, emulsion ripening rate, emulsion stability, composition, toxicity, biocompatibility, therapeutic effectiveness, therapeutic agent delivery or release rate, immune or other physiological response or any combination of these. In various embodiments, for example, an emulsion does not contain a vegetable oil component, such as a soy bean oil component. In certain embodiments, for example, an emulsion does not support bacterial growth. In some embodiments, for example, an emulsion does not contain a lipid component. In some embodiments, for example, an emulsion does not contain a phospholipid component, such as an egg phospholipid component.

In embodiments, the composition and relative amounts of the components of the emulsions are selected so as to achieve a desired solubilization amount of one or more hydrophobic therapeutic agents, such as a clinically or therapeutically effective amount. In embodiments, the composition and relative amounts of the components of the emulsions are selected so as to achieve a desired or controlled release rate, release timing or targeted delivery of one or more hydrophobic therapeutic agents.

In embodiments, emulsions of the invention comprise semi-fluorinated block copolymers. The structure, composition, size or concentration of the semi-fluorinated block copolymers and polymer block components thereof are optionally selected so as to provide certain properties to the emulsion, such as physical properties, emulsion ripening rate, emulsion stability, therapeutic agent solubility, composition, toxicity, biocompatibility, therapeutic effectiveness, therapeutic agent delivery rate or release rate, immune or other physiological response or any combination of these. In an embodiment, the hydrophilic block and fluorophilic block as each independently polymer terminating blocks, for example, wherein the hydrophobic block is an intermediate block provided directly or indirectly in between the hydrophilic block and fluorophilic block. In embodiments, for example, the semi-fluorinated block copolymers have a concentration selected from the range of 1 mg mL$^{-1}$ to 50 mg mL$^{-1}$, optionally for some applications selected from the range of 5 mg mL$^{-1}$ to 50 mg mL$^{-1}$. In some embodiments, the semi-fluorinated block copolymers have a concentration selected from the range of 10 to 50 mg mL$^{-1}$. In embodiments, for example, each of the semi-fluorinated block copolymers independently have a molecular weight selected from the range 100 Da to 20,000 Da, and optionally for some applications 1100 Da to 14,000 Da.

In certain embodiments, the structure, composition or size of the hydrophilic block of the semi-fluorinated block copolymers are selected so as to make stable emulsion-based formulations from a wide range of hydrophobic therapeutic agents, such as hydrophobic anesthetics. In exemplary embodiments, the hydrophilic block of each of the semi-fluorinated block copolymers is a polymer terminating group. In embodiments, the hydrophilic block is selected from the group consisting of a polyoxygenated polymer block, a polysaccharide block and a chitosan derivative block. In an embodiment, the hydrophilic block is a polyoxygenated block, such as a poly(ethylene glycol) block. In exemplary embodiments, the hydrophilic block is a poly(ethylene glycol) block, for example, having a molecular weight selected from the range of 500 g mol$^{-1}$ to 20,000 g mol$^{-1}$, optionally for some applications selected from the range of 1000 g mol$^{-1}$ to 20,000 g mol$^{-1}$, optionally for some applications selected from the range of 1000 g mol$^{-1}$ to 15,000 g mol$^{-1}$, and optionally for some applications selected from the range of 1000 g mol$^{-1}$ to 10,000 g mol$^{-1}$. In some embodiments, selection of the size/molecular weight of the poly(ethylene glycol) block establishes the release rate of a hydrophobic therapeutic agent and/or stability of the nanoemulsion with respect to ripening, coagulation and phase separation processes. In some embodiments, the hydrophilic block is directly linked to the hydrophobic block.

In certain embodiments, the structure, composition or size of the fluorophilic block of the semi-fluorinated block copolymers are selected so as to make stable emulsion-based formulations from a wide range of hydrophobic therapeutic agents, such as hydrophobic anesthetics. In exemplary embodiments, the fluorophilic block is a fluorocarbon moiety having at least 7 carbon-fluorine bonds, and optionally for some embodiments, at least 13 carbon-fluorine bonds, and optionally for some embodiments at least 21 carbon-fluorine bonds. For example, in one embodiment, the fluorophilic block is a polymer terminating group. In exemplary embodiments, the fluorophilic block is a fluorocarbon moiety having between 3 to 50 carbon-fluorine bonds, optionally for some applications 13 to 50 carbon-fluorine bonds, and optionally for some applications 3 to 31 carbon-fluorine bonds. In some embodiments, the fluorophilic block is a fluorinated alkyl group having a length greater than or equal to 3 carbons and optionally for some applications greater than or equal to 6 carbons, and optionally for some embodiments greater than or equal to 10 carbons. In some embodiments, the fluorophilic block is a fluorinated alkyl group having a length of 3 to 20 carbons, optionally for some applications of 3 to 15 carbons and optionally for some applications 6 to 15 carbons. In some embodiments, for example, the fluorophilic block is a perfluorinated alkyl group having a length of 3 to 15 carbons, and optionally 3 to 8 carbons. In exemplary embodiments, the fluorophilic block is directly linked to the hydrophobic block. In some embodiments, for example, the fluorophilic block, the hydrophilic block or both are independently linked to the hydrophobic block via a linking moiety having 1 to 10 carbons, such as a $C_1$-$C_{10}$ ether group, a carbamate group, an amide group, an alkylene group or amino group.

In certain embodiments, the structure, composition or size of the hydrophobic block of the semi-fluorinated block copolymers are selected so as to make stable emulsion-based formulations from a wide range of hydrophobic therapeutic agents, such as hydrophobic anesthetics. In embodiments, for example, the hydrophobic block is selected from the group consisting of a $C_5$-$C_{20}$ alkylene group, a poly(ε-caprolactone) block, a poly(lactic acid) block; a poly(propylene glycol) block; a poly(amino acid) block; a poly(ester) block and poly(lactic-co-glycolic acid). In some embodiments, the hydrophobic block is an unsubstituted $C_5$-$C_{20}$ alkylene group, optionally an unsubstituted $C_5$-$C_{10}$ alkylene group. In an exemplary embodiment, the hydrophobic block is a group corresponding to an hexyl, heptyl, octyl, nonyl, decyl, undecyl or dodecyl group. In some embodiments, the hydrophobic block is an unsubstituted alkylene group having at least 5 carbons, optionally for some applications at least 8 carbons and optionally for some applications at least 10 carbons. In an exemplary embodiment, the hydrophobic block is derived from a phospholipid hydrophobic group, such as a glycerophospholipid. In an exemplary embodiment, the hydrophobic block is derived from distearoyl-glycero-phosphoethanolamine, such as 1,2-distearoyl-S,N-glycero-3-phosphoethanolamine (DSPE).

In a specific embodiment, each of the semi-fluorinated block copolymers independently has the formula (FX1):

(FX1)

where A is the hydrophilic block, B is the hydrophobic block and D is the fluorophilic block; where $L^1$ and $L^2$ are each independently a linking group; and where m is 0 or 1 and n is 0 or 1. For embodiments where m is 0, $L^1$ is not present and A and B are directly bonded to one another. For embodiments where n is 0, $L^2$ is not present and B and D are directly bonded to one another.

In certain embodiments each of the semi-fluorinated block copolymers independently has the formula (FX1), wherein A is $—(CH_2CH_2O)_qR^1$, where $R^1$ is hydrogen, methyl, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ alkoxy or $C_1$-$C_{10}$ acyl and q is an integer selected from the range of 10 to 300, and optionally for some applications 20 to 100 and optionally for some applications 20 to 50. In certain embodiments each of the semi-fluorinated block copolymers independently has the formula (FX1), wherein B is $—(CH_2)_o—$, where o is an integer selected from the range of 5 to 30, and optionally for some applications 5 to 20, and optionally for some applications 8 to 15. In certain embodiments each of the semi-fluorinated block copolymers independently has the formula (FX1), wherein D is $—(CF_2)_pR^2$, where $R^2$ is hydrogen, halo or $C_1$-$C_5$ alkyl and p is an integer selected from the range of 3 to 20, and optionally for some embodiments 3 to 15 and optionally for some embodiments 6 to 15.

In a specific embodiment, each of the semi-fluorinated block copolymers independently has the formula (FX2):

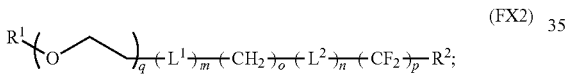

(FX2)

wherein q is an integer selected from the range of 10 to 300, o is an integer selected from the range of 5 to 20, and p is an integer selected from the range of 3 to 15; wherein $R^1$ is hydrogen, methyl, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ alkoxy or $C_1$-$C_{10}$ acyl; where $R^2$ is hydrogen, halo or $C_1$-$C_5$ alkyl; wherein each of $L^1$ and $L^2$ is independently $—(CH_2)_e—$, $—(CH_2)_eO(CH_2)_f—$, $—(CH_2)_eS(CH_2)_f—$, $—(CH_2)_eNR^{11}(CH_2)_f—$, $—(CH_2)_eOCONR^{12}(CH_2)_f—$, $—(CH_2)_eCONR^{13}(CH_2)_f—$, $—(CH_2)_eNR^{14}COO(CH_2)_f—$, $—(CH_2)_eNR^{15}CO(CH_2)_f—$ or $—(CH_2)_eNR^{16}CONR^{17}(CH_2)_f—$; wherein each of $R^{11}$-$R^{17}$ is independently hydrogen, methyl, or $C_1$-$C_5$ alkyl; wherein each of e and f is independently an integer selected from the range of 0 to 5 and wherein m is 0 or 1 and n is 0 or 1. In a specific embodiment, the semi-fluorinated block copolymers independently has the formula (FX2) and, a halogen is selected from the group consisting of F, Cl and Br. In a specific embodiment, when e is 0, the $(CH_2)_e$ group is not present and moieties adjacent to the $(CH_2)_e$ group in the above described structures for $L^1$ and $L^2$ are directly bonded to one another. In a specific embodiment, when f is 0, the $(CH_2)_f$ group is not present and moieties adjacent to the $(CH_2)_f$ group in the above described structures for $L^1$ and $L^2$ are directly bonded to one another.

In some embodiments, the semi-fluorinated block copolymers independently has the formula (FX2), wherein q is an integer selected from the range of 10 to 200, and optionally for some applications 10 to 100 and optionally for some applications 10 to 50. In some embodiments, the semi-fluorinated block copolymers independently has the formula (FX2), wherein o is an integer selected from the range of 5 to 16, and optionally for some applications 8 to 16. In some embodiments, the semi-fluorinated block copolymers independently has the formula (FX2), wherein p is an integer selected from the range of 5 to 15, and optionally for some applications 8 to 15. In some embodiments, the semi-fluorinated block copolymers independently has the formula (FX2), wherein $R^1$ is hydrogen, $C_1$-$C_{10}$ alkoxy or $C_1$-$C_{10}$ alkyl, and optionally methyl or methoxy. In some embodiments, the semi-fluorinated block copolymers independently has the formula (FX2), wherein $R^2$ is hydrogen or halo, optionally F. In some embodiments, the semi-fluorinated block copolymers independently has the formula (FX2), wherein each of $R^{11}$-$R^{17}$ is independently hydrogen or $C_1$-$C_5$ alkyl, optionally methyl.

In a specific embodiment, $L^1$ is $—O—$. In a specific embodiment, $L^2$ is $—OCH_2—$. In a specific embodiment, each of the semi-fluorinated block copolymers independently has the formula (FX3A) or (FX3B):

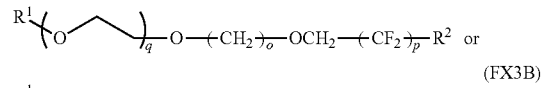

(FX3A)

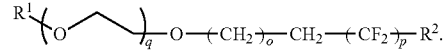

(FX3B)

In a specific embodiment, $R^1$ is $—CH_3$. In a specific embodiment, $R^2$ is $—F$. In a specific embodiment, each of the semi-fluorinated block copolymers independently has the formula (FX4A) or (FX4B):

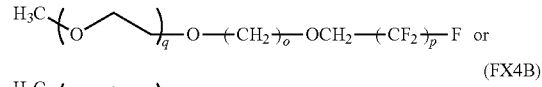

(FX4A)

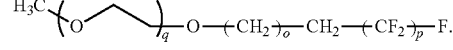

(FX4B)

In an exemplary embodiment, each of the semi-fluorinated block copolymers independently has the formula (FX5A) or (FX5B):

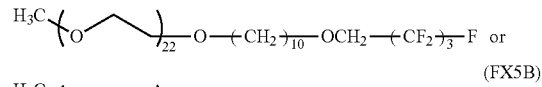

(FX5A)

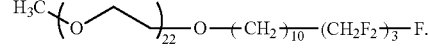

(FX5B)

In embodiments, the semi-fluorinated block copolymers comprise a branched structure, such as a structure where one or more polymer blocks are polymer terminating groups bonded directly or indirectly to a common carbon center. For example in one embodiment, the fluorophilic block and the hydrophobic block of each of the semi-fluorinated block copolymers are independently polymer terminating groups. In a specific embodiment, for example, the fluorophilic block is linked to the hydrophobic block and the hydrophilic block via a polymer branch group, such as a branch group having the structure:

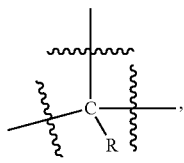

wherein R is hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ alkoxy, or $C_1$-$C_{10}$ acyl, and optionally wherein R is hydrogen or $C_1$-$C_5$ alkyl, and optionally wherein R is hydrogen or methyl. In a specific embodiment, for example, the fluorophilic block is linked to the hydrophobic block and the hydrophilic block via a polymer branch group, such as a branch group having the structure:

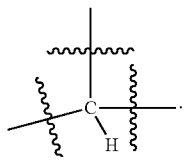 [SMILES: *C(*)*]

In an exemplary embodiment, each of the semi-fluorinated block copolymers independently has the formula (FX6):

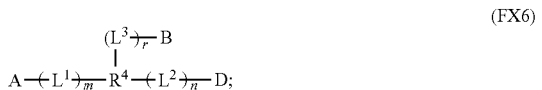

(FX6)

where A is the hydrophilic block, B is the hydrophobic block and D is the fluorophilic block; where $R^4$ is a polymer branch group; where $L^1$, $L^2$ and $L^3$ are each independently a linking group; and where m is 0 or 1, n is 0 or 1 and r is 0 or 1. For embodiments where m is 0, $L^1$ is not present and A and $R^4$ are directly bonded to one another. For embodiments where n is 0, $L^2$ is not present and $R^4$ and D are directly bonded to one another. For embodiments where r is 0, $L^3$ is not present and B and $R^4$ are directly bonded to one another.

In certain embodiments each of the semi-fluorinated block copolymers independently has the formula (FX6), wherein A is —$(CH_2CH_2O)_qR^1$, where $R^1$ is hydrogen, methyl, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ alkoxy or $C_1$-$C_{10}$ acyl and q is an integer selected from the range of 10 to 300, and optionally for some applications 20 to 100 and optionally for some applications 20 to 50. In certain embodiments each of the semi-fluorinated block copolymers independently has the formula (FX6), wherein B is —$(CH_2)_oR^3$, wherein $R^3$ is hydrogen, methyl, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ alkoxy or $C_1$-$C_{10}$ acyl and o is an integer selected from the range of 5 to 30, and optionally for some applications 5 to 20, and optionally for some applications 8 to 15. In certain embodiments each of the semi-fluorinated block copolymers independently has the formula (FX6), wherein D is —$(CF_2)_pR^2$, where $R^2$ is hydrogen, halo or $C_1$-$C_5$ alkyl and p is an integer selected from the range of 3 to 20, and optionally for some embodiments 3 to 15 and optionally for some embodiments 6 to 15.

In exemplary embodiments, each of the semi-fluorinated block copolymers independently has the formula (FX7):

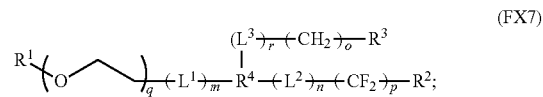

(FX7)

where q is an integer selected from the range of 10 to 300, o is an integer selected from the range of 5 to 20, and p is an integer selected from the range of 3 to 15; where each of $R^1$ and $R^3$ is independently hydrogen, methyl, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ alkoxy, or $C_1$-$C_{10}$ acyl; where $R^2$ is hydrogen, halo or $C_1$-$C_5$ alkyl; where each of $L^1$, $L^2$ and $L^3$ is independently —$(CH_2)_e$—, —$(CH_2)_eO(CH_2)_f$—, —$(CH_2)_eS(CH_2)_f$—, —$(CH_2)_eNR^{11}(CH_2)_f$—, —$(CH_2)_eOCONR^{12}(CH_2)_f$—, —$(CH_2)_eCONR^{13}(CH_2)_f$—, —$(CH_2)_eNR^{14}COO(CH_2)_f$—, —$(CH_2)_eNR^{15}CO(CH_2)_f$— or —$(CH_2)_eNR^{16}CONR^{17}(CH_2)_f$—; where each of $R^{11}$-$R^{17}$ is independently hydrogen, methyl, or $C_1$-$C_5$ alkyl; where each of e and f is independently an integer selected from the range of 0 to 5; and wherein m is 0 or 1, n is 0 or 1 and r is 0 or 1. In a specific embodiment each of the semi-fluorinated block copolymers independently has the formula (FX7), wherein a halogen is selected from the group consisting of F, Cl and Br. In a specific embodiment, when e is 0, the $(CH_2)_e$ group is not present and moieties adjacent to the $(CH_2)_e$ group in the above described structures for $L^1$, $L^2$ and $L^3$ are directly bonded to one another. In a specific embodiment, when f is 0, the $(CH_2)_f$ group is not present and moieties adjacent to the $(CH_2)_f$ group in the above described structures for $L^1$, $L^2$ and $L^3$ are directly bonded to one another.

In some embodiments, the semi-fluorinated block copolymers independently has the formula (FX7), wherein q is an integer selected from the range of 10 to 200, and optionally for some applications 10 to 100 and optionally for some applications 10 to 50. In some embodiments, the semi-fluorinated block copolymers independently has the formula (FX7), wherein o is an integer selected from the range of 5 to 16, and optionally for some applications 8 to 16. In some embodiments, the semi-fluorinated block copolymers independently has the formula (FX7), wherein p is an integer selected from the range of 5 to 15, and optionally for some applications 8 to 15. In some embodiments, the semi-fluorinated block copolymers independently has the formula (FX7), wherein $R^1$ is hydrogen, $C_1$-$C_{10}$ alkoxy or $C_1$-$C_{10}$ alkyl, and optionally methyl or methoxy. In some embodiments, the semi-fluorinated block copolymers independently has the formula (FX7), wherein $R^2$ is hydrogen or halo, optionally F. In some embodiments, the semi-fluorinated block copolymers independently has the formula (FX7), wherein $R^3$ is hydrogen, $C_1$-$C_{10}$ alkoxy or $C_1$-$C_{10}$ alkyl, and optionally methyl or methoxy In some embodiments, the semi-fluorinated block copolymers independently has the formula (FX7), wherein each of $R^{11}$-$R^{17}$ is independently hydrogen or $C_1$-$C_5$ alkyl, optionally methyl. In some embodiments, the semi-fluorinated block copolymers independently has the formula (FX7), wherein m is 0. In some embodiments, the semi-fluorinated block copolymers independently has the formula (FX7), wherein r is 0. In some embodiments, the semi-fluorinated block copolymers independently has the formula (FX7), wherein n is 0.

In a specific embodiment, $L^1$ is —$OCH_2$—. In a specific embodiment, $L^2$ is —$OCH_2$—. In a specific embodiment, $L^3$ is —O—. Combinations of any of the above described embodiments are possible and expressly included with the present disclosure.

In exemplary embodiments, each of the semi-fluorinated block copolymers independently have the formula (FX8A) or (FX8B):

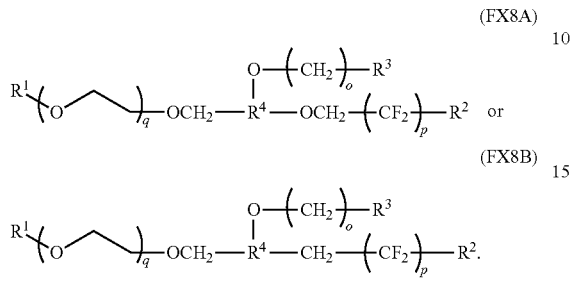

In exemplary embodiments, each of the semi-fluorinated block copolymers independently has the formula (FX9A) or (FX9B):

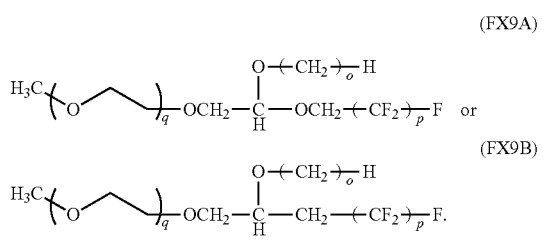

In exemplary embodiments, each of the semi-fluorinated block copolymers independently has the formula (FX10):

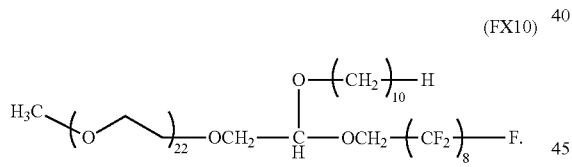

In certain embodiments, the structure, composition, size or concentration of the phospholipid surfactant of emulsions of the invention is selected so as to make stable emulsion-based formulations from a wide range of hydrophobic therapeutic agents, such as hydrophobic anesthetics. In embodiments, the structure, composition, size or concentration of the phospholipid surfactant are selected so as to provide certain properties to the emulsion, such as physical properties, emulsion ripening rate, emulsion stability, therapeutic agent solubility, composition, toxicity, biocompatibility, therapeutic effectiveness, therapeutic agent delivery rate or release rate, immune or other physiological response or any combination of these. For example, in one embodiment, the phospholipid surfactant has a concentration of 10 mg mL$^{-1}$ to 20 mg mL$^{-1}$ in the emulsion.

A variety of phospholipid surfactants are useful with the emulsions of the invention. In one embodiment, the phospholipid surfactant is a naturally occurring phospholipid. In exemplary embodiments, the phospholipid surfactant is an egg phospholipid. In a specific embodiment, the phospholipid surfactant is Lipoid 80.

In embodiments, for example, the phospholipid surfactant has the formula (FX11):

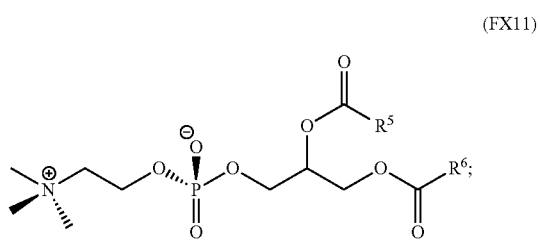

where each of $R^5$ and $R^6$ is independently hydrogen, $C_5$-$C_{20}$ alkyl, $C_5$-$C_{20}$ cycloalkyl, $C_5$-$C_{30}$ aryl, $C_5$-$C_{30}$ heteroaryl, $C_5$-$C_{20}$ acyl, $C_5$-$C_{20}$ alkenyl, $C_5$-$C_{20}$ cycloalkenyl, $C_5$-$C_{20}$ alkynyl, or $C_5$-$C_{20}$ alkylaryl. In an embodiment, the phospholipid surfactant has the formula (FX11), wherein $R^5$ and $R^6$ are each independently $C_5$-$C_{20}$ alkyl, optionally $C_5$-$C_{10}$ alkyl.

In embodiments, the phospholipid surfactant has the formula (FX12):

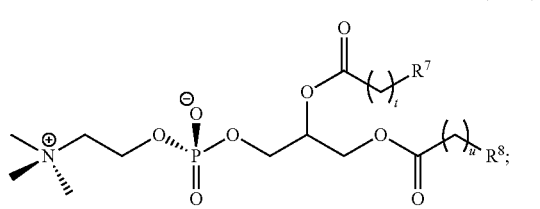

where each of t and u is independently an integer select from the range of 5 to 35; wherein each of $R^7$ and $R^8$ is independently hydrogen, $C_5$-$C_{20}$ alkyl, $C_5$-$C_{20}$ cycloalkyl, $C_5$-$C_{30}$ aryl, $C_5$-$C_{30}$ heteroaryl, $C_5$-$C_{20}$ acyl, $C_5$-$C_{20}$ alkenyl, $C_5$-$C_{20}$ cycloalkenyl, $C_5$-$C_{20}$ alkynyl, or $C_5$-$C_{20}$ alkylaryl. In an embodiment, the phospholipid surfactant has the formula (FX12), wherein $R^7$ and $R^8$ are each independently $C_5$-$C_{20}$ alkyl, optionally $C_5$-$C_{10}$ alkyl.

In a specific embodiment, the phospholipid surfactant has the formula (FX13):

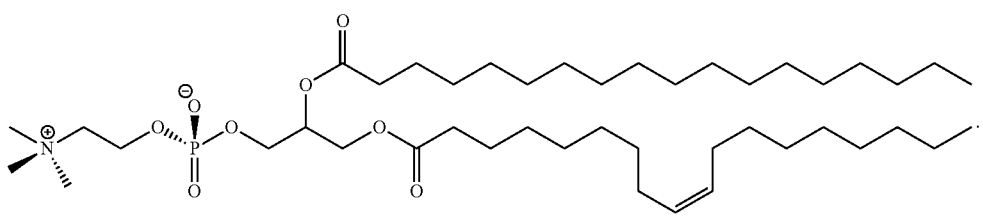

A variety of therapeutic agents are useful with the emulsions of the invention. In certain embodiments, the structure, composition, size or concentration of the therapeutic agent is selected so as to make a stable emulsion-based formulation. In embodiments, the structure, composition, size or concentration of the therapeutic agent are selected so as to provide certain properties to the emulsion, such as physical properties, emulsion ripening rate, emulsion stability, therapeutic agent solubility, composition, toxicity, biocompatibility, therapeutic effectiveness, therapeutic agent delivery rate or release rate, immune or other physiological response or any combination of these. In an embodiment, for example, the therapeutic agent has a concentration of at least 0.2 mg mL$^{-1}$. In an embodiment, for example, the therapeutic agent has a concentration of 0.2 to 50 mg mL$^{-1}$, optionally for some applications a concentration of 1 to 50 mg mL$^{-1}$, in the emulsion. In an embodiment, the therapeutic agent has a concentration selected from the range of 0.2 mg mL$^{-1}$ to 30 mg mL$^{-1}$ in the emulsion.

In certain embodiments, the therapeutic agent is a hydrophobic compound. Use of hydrophobic therapeutic agents is beneficial as a variety of hydrophobic therapeutic agents exhibit reduced toxicity, increased therapeutic effectiveness or smaller required therapeutic dosages as compared to some non-hydrophobic therapeutic agents. In addition, therapeutic agents for a desired clinical application may only be available as a hydrophobic compound. In embodiments, emulsions of the invention are, thus, particularly useful for providing a therapeutically deliverable quantity of a hydrophobic therapeutic agent in order to achieve a desired clinical outcome, such as anesthesia. In an embodiment, for example, the hydrophobic compound is characterized by a solubility in water of equal to or less than 5 mM, optionally for some applications equal to or less than 1 mM and optionally equal to or less than 0.7 mM. For reference, the solubility of propofol in water is 0.124 mg/ml corresponding to 0.696 mM.

In a specific embodiment, the hydrophobic compound is noncovalently associated with the hydrophobic block, the fluorophilic block or both the hydrophobic block and the fluorophilic block of the semi-fluorinated block copolymers. For example, in embodiments, the hydrophobic compound is dissolved or solvated by a hydrophobic block, a fluorophilic block or both, such that the hydrophobic compound is suspended or otherwise deliverable by an emulsion of the invention.

A variety of hydrophobic compounds are useful with the emulsions of the invention. In a specific embodiment, the hydrophobic compound is a hydrophobic drug. In a specific embodiment, the hydrophobic compound is an anesthetic drug. In embodiments, the hydrophobic compound is a substituted or unsubstituted aromatic compound or a substituted or unsubstituted heteroaromatic compound. In a specific embodiment, for example, the hydrophobic compound is a neurosteroid drug. In exemplary embodiments, the anesthetic drug is propofol or alfaxalone. Optionally, the anesthetic drug has a concentration of 5 mg mL$^{-1}$ to 50 mg mL$^{-1}$ in the emulsion. Optionally, the anesthetic drug is propofol provided at a concentration of 5 mg mL$^{-1}$ to 50 mg mL$^{-1}$ in the emulsion.

In a specific embodiment, the hydrophobic compound is not a fluorinated anesthetic compound. In a specific embodiment, the hydrophobic compound is not sevoflurane. In a specific embodiment, the hydrophobic compound is not isoflurane. In a specific embodiment, the hydrophobic compound is not desflurane. In a specific embodiment, the hydrophobic compound is not enflurane. In a specific embodiment, the hydrophobic compound is not methoxyflurane.

As described above, the present invention provides emulsions, such as emulsions comprising a continuous phase and a dispersed phase. In certain embodiments, the aqueous solution of the continuous phase comprises a saline solution. In embodiments, for example, the aqueous solution of the continuous phase is isotonic to blood plasma. In an embodiment, the dispersed phase comprises a plurality of droplets dispersed in the continuous phase. In embodiments, for example, the droplets dispersed in the continuous phase comprise self-assembled supramolecular structures. Various emulsion embodiments do not include micelle-based solutions, but instead comprise droplets of the dispersed phase suspended in the continuous phase.

In some embodiments, for example, the droplets have a hydrophilic exterior shell comprising the hydrophilic blocks of the semi-fluorinated block copolymers. In some embodiments, for example, the droplets have a hydrophobic intermediate shell comprising the hydrophobic blocks of the semi-fluorinated block copolymers. In some embodiments, for example, the droplets have a fluorophilic core. In exemplary embodiments, for example, the hydrophobic compound is noncovalently associated with the hydrophobic intermediate shell.

In a specific embodiment, an exemplary emulsion of the invention comprises the hydrophobic compound at a concentration selected from the range of 0.1 to 100 mg mL$^{-1}$, optionally for some applications 0.2 to 50 mg mL$^{-1}$, the phospholipid surfactant at a concentration selected from the range of 1 to 50 mg mL$^{-1}$; optionally for some applications 10 to 20 mg mL$^{-1}$; and the semi-fluorinated block copolymers at a concentration selected from the range of 1 to 100 mg mL$^{-1}$, optionally 10 to 50 mg mL$^{-1}$. In a specific embodiment, an exemplary emulsion of the invention comprises the hydrophobic compound at a concentration selected from the range of 0.1 to 100 mg mL$^{-1}$, optionally for some applications 0.2 to 50 mg mL$^{-1}$; and the semi-fluorinated block copolymers at a concentration selected from the range of 1 to 100 mg mL$^{-1}$, optionally 10 to 50 mg mL$^{-1}$. Exemplary emulsion embodiments are useful for administration to a patient in need thereof via intravenous injection.

Emulsions of embodiments of the invention are stable and possess a shelf life such that the emulsions do not quickly settle into two or more phases and thus are suitable for administration to a patient or subject at a time period after the emulsion is prepared or manufactured, such as a time period greater than 1 day or greater than 1 month. In an exemplary embodiment, the droplets do not undergo an appreciable change in size over a period of 1 day to 4 weeks. In embodiments, for example, an appreciable change in size is a change that is greater than or equal to a 10% increase.

For certain embodiments, an emulsion of the invention comprises a nanoemulsion. For example, in some embodiments, the emulsion comprises droplets having an average diameter selected from the range of 1 nm to 500 nm. For example, in some embodiments, the emulsion comprises droplets having an average diameter less than 1000 nm. In some embodiments, the emulsion comprises droplets having an average diameter less than 400 nm. For some embodiments, the emulsion does not comprise micelles. For some embodiments, the emulsion does not comprise vesicles. In certain embodiments, the emulsion is not a microemulsion. For some embodiments, the emulsion comprises a supramolecular structure. For other embodiments, the emulsion does not comprise a supramolecular structure.

In an aspect, the invention provides an emulsion, such as a nanoemulsion comprising (i) semifluorinated copolymers having a branched structure wherein the hydrophilic block comprises a first branch, the hydrophobic block comprises a second branch and the fluorophilic block comprises a third branch; a therapeutic agent comprising a hydrophobic compound; and a perhalogenated fluorous compound. In an embodiment, for example, the perhalogenated fluorous compound. is an emulsion stabilizing additive. In an embodiment, for example, the perhalogenated fluorous compound is 5% to 20% by volume of the emulsion. In an embodiment, for example, the perhalogenated fluorous compound has 12 to 25 carbon-fluorine bonds. In an embodiment, for example, the perhalogenated fluorous compound is a substituted or unsubstituted fluorocarbon having a length of 4 to 20 carbons. In an embodiment, for example, the substituted or unsubstituted fluorocarbon is linear, branched or cyclic. In an embodiment, for example, the substituted or unsubstituted fluorocarbon is a substituted or unsubstituted $C_4$-$C_{20}$ fluoroalkane. In an embodiment, for example, the perhalogenated fluorous compound has a solubility in water less than or equal to 20 nanomolar. In an embodiment, for example, the perhalogenated fluorous compound has a molecular weight over the range of 460 amu to 920 amu. In an embodiment, for example, the perhalogenated fluorous compound is selected from the group consisting of: a perfluorocarbon; a bromine substituted perfluorocarbon; a chlorine substituted perfluorocarbon; and a bromine and chlorine substituted perfluorocarbon. In an embodiment, for example, the perhalogenated fluorous compound is selected from the group consisting of perfluorooctyl bromide, perfluorononyl bromide, perfluorodecyl bromide, perfluorodecalin, perfluorodichlorooctane, bis-perfluorobutyl ethylene and perfluoro(methyldecalin). In an embodiment, for example, the perhalogenated fluorous compound is perfluorooctyl bromide or perfluorodecalin.

In another aspect, the present invention provides methods. A method of this aspect comprises a method of delivering a therapeutic agent to a patient in need thereof. In an embodiment, such a method comprises, for example, the steps of: providing an emulsion comprising: an aqueous solution; semi-fluorinated block copolymers; a therapeutic agent comprising a hydrophobic compound; and a phospholipid surfactant; wherein each of the semi-fluorinated block copolymers independently comprises a hydrophilic block, a hydrophobic block and a fluorophilic block; wherein the hydrophobic block of each of the semi-fluorinated block copolymers is provided between the fluorophilic block and the hydrophilic block; wherein the emulsion comprises a continuous phase and a dispersed phase, wherein the continuous phase comprises the aqueous solution and the dispersed phase comprises the semi-fluorinated block copolymers, the therapeutic agent and the phospholipid surfactant; and administering the emulsion to the patient, wherein the therapeutic agent is released from the emulsion, thereby delivering the therapeutic agent to the patient in need thereof.

In an embodiment, a method of delivering a therapeutic agent to a patient in need thereof comprises the steps of: providing an emulsion comprising: an aqueous solution; semi-fluorinated block copolymers; and a therapeutic agent comprising a hydrophobic compound; wherein each of the semi-fluorinated block copolymers independently comprises a hydrophilic block, a hydrophobic block and a fluorophilic block; wherein each of the semi-fluorinated block copolymers has a branched structure wherein the hydrophilic block comprises a first branch, the hydrophobic block comprises a second branch and the fluorophilic block comprises a third branch; wherein the emulsion comprises a continuous phase and a dispersed phase, wherein the continuous phase comprises the aqueous solution and the dispersed phase comprises the semi-fluorinated block copolymers and the therapeutic agent; and administering the emulsion to the patient, wherein the therapeutic agent is released from the emulsion, thereby delivering the therapeutic agent to the patient in need thereof.

In exemplary embodiments, an emulsion administered to a patient comprises any of the emulsions described previously herein. In a specific embodiment, an emulsion administered to a patient is a nanoemulsion. In a specific embodiment, the hydrophobic compound administered to a patient is a hydrophobic drug, such as an anesthetic drug, for example propofol.

In exemplary embodiments of methods of this aspect, the step of administering the emulsion provides for controlled release of the hydrophobic drug from the emulsion. Optionally, the step of administering the emulsion is carried out via intravenous injection. In a specific embodiment, a volume of the emulsion less than or equal to 500 mL is administered to the patient. In exemplary embodiments, a volume of the emulsion selected from the range 0.1 mL to 50 mL is administered to the patient. In a specific embodiment, the emulsion is delivered to the patient at a rate less than or equal to 100 mL per minute. In exemplary embodiments, the emulsion is delivered to the patient at a rate selected from the range of 0.01 to 100 mL per minute.

In a further aspect, provided are methods of making emulsions. In exemplary embodiments, the emulsion is a nanoemulsion. An exemplary method of this aspect comprises the steps of: providing a therapeutic formulation comprising: an aqueous solution; semi-fluorinated block copolymers; wherein each of the semi-fluorinated block copolymers independently comprises a hydrophilic block, a hydrophobic block and a fluorophilic block; wherein the hydrophobic block of each of the semi-fluorinated block copolymers is provided between the fluorophilic block and the hydrophilic block; a therapeutic agent comprising a hydrophobic compound; and a phospholipid surfactant; and emulsifying the therapeutic formulation, thereby making an emulsion comprising a continuous phase and a dispersed phase, wherein the continuous phase comprises the aqueous solution and the dispersed phase comprises the semi-fluorinated block copolymers, the therapeutic agent and the phospholipid surfactant.

Another exemplary method of this aspect comprises the steps of: providing a therapeutic formulation comprising: an aqueous solution; semi-fluorinated block copolymers; wherein each of the semi-fluorinated block copolymers independently comprises a hydrophilic block, a hydrophobic block and a fluorophilic block; wherein each of the semi-fluorinated block copolymers has a branched structure wherein the hydrophilic block comprises a first branch, the hydrophobic block comprises a second branch and the fluorophilic block comprises a third branch; and a therapeutic agent comprising a hydrophobic compound; and emulsifying the therapeutic formulation, thereby making an emulsion comprising a continuous phase and a dispersed phase, wherein the continuous phase comprises the aqueous solution and the dispersed phase comprises the semi-fluorinated block copolymers and the therapeutic agent.

In certain embodiments of methods of this aspect, the step of emulsifying the therapeutic formulation comprises the steps of: adding the hydrophobic compound and the phospholipid surfactant to the aqueous solution having the semifluorinated block copolymers therein, thereby generating a mixture; and homogenizing the mixture, thereby generating the emulsion. In certain embodiments of methods of this aspect, the step of emulsifying the therapeutic formulation comprises the steps of: adding the hydrophobic compound to the aqueous solution having the semi-fluorinated block copolymers therein, thereby generating a mixture; and homogenizing the mixture, thereby generating the emulsion.

In exemplary embodiments, methods of this aspect further comprise a step of lowering a temperature of the mixture during the step of homogenizing the mixture. In embodiments, for example, the step of homogenizing the mixture is carried out using a low-energy mixer, a microfluidizer or both. Low-energy mixers are known in the art, such described in AIChE J., 57: 27-39. doi: 10.1002/aic.12253.

In an aspect, the invention provides a method of accelerating emergence from anesthesia in a subject that has received an anesthetic drug, the method comprising the step of: (i) administering to the subject a clinically effective amount of a lipid emulsion.

In an embodiment, for example, the lipid emulsion comprises a lipid component that is a glyceride or derivative thereon. In an embodiment, for example, the lipid component comprises a triglyceride or derivative thereon. In an embodiment, for example, the lipid component comprises one or more vegetable oil or derivative thereof. In an embodiment, for example, the lipid component comprises soy bean oil. In an embodiment, for example, the lipid emulsion comprises a phospholipid component. In an embodiment, for example, the a phospholipid component comprises an egg phospholipid. In an embodiment, for example, the lipid emulsion comprises a glycerin component. In an embodiment, for example, the lipid emulsion comprises Intralipid® or a modification thereof.

In an embodiment, for example, the clinically effective amount of the lipid emulsion is selected from the range of 0.1 mL/kg to 10 mL/kg, optionally for some applications 0.1 mL/kg to 5 mL/kg and optionally for some applications 0.1 mL/kg to 2 mL/kg. In an embodiment, for example, the volume of emulsion corresponding to an clinically effective dose is 100 ml or less. In an embodiment, for example, the method of this aspect comprises administering one or more bolus doses of the lipid emulsion to the subject. In an embodiment, for example, each of the bolus doses of the lipid emulsion is independently selected from the range of 0.1 mL/kg to 15 mL/kg, optionally for some applications 0.1 mL/kg to 2 mL/kg and optionally for some applications 0.1 mL/kg to 1 mL/kg. In an embodiment, for example, each of the bolus doses of the lipid emulsion is independently administered over a time period selected from the range of 1 second to 5 minutes, optionally for some applications 30 seconds to 2 minutes, and optionally for some applications 30 seconds to 1 minutes. In an embodiment, for example, the one or more bolus doses of the lipid emulsion is administered after administration of an induction dose of the anesthetic drug is administered to the subject or after a maintenance dose of the anesthetic drug is administered to the subject.

In an embodiment, for example, the anesthetic drug is a hydrophobic compound. In an embodiment, for example, the hydrophobic compound is characterized by a solubility in water equal to or less than 0.7 mM. In an embodiment, for example, the anesthetic drug is a lipid soluble compound. In an embodiment, for example, the anesthetic drug is propofol or alfaxalone.

In an embodiment, for example, a method of this aspect provides an increase in the rate of the emergence from anesthesia of the subject greater than or equal to a factor of 1.5. In an embodiment, for example, a method of this aspect provides an increase in the clearance of the anesthetic drug.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

STATEMENTS REGARDING CHEMICAL COMPOUNDS AND NOMENCLATURE

Figure 1A:
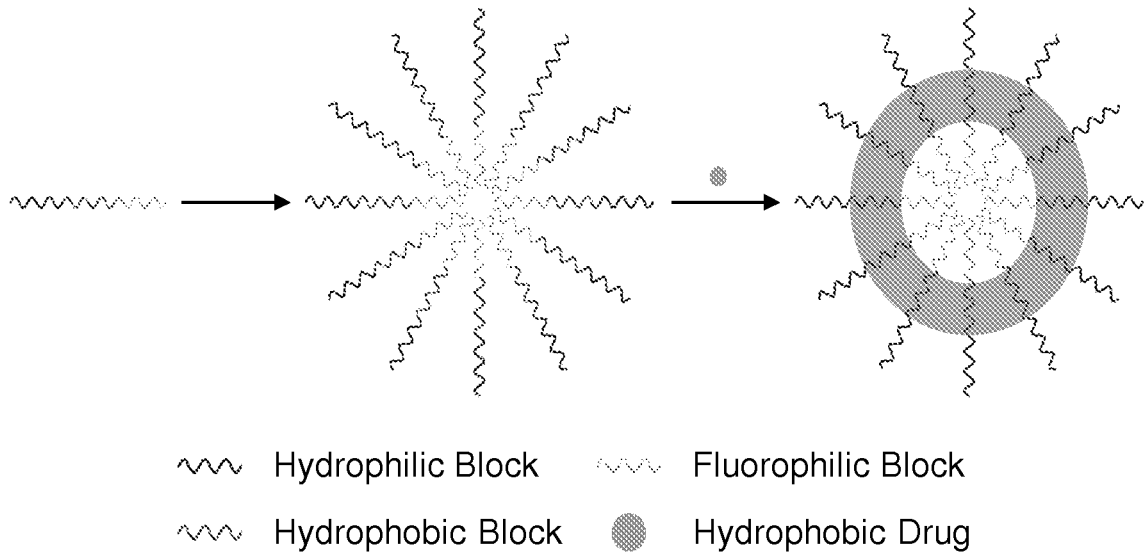
FIG. 1A provides a schematic illustration of the formation of dispersed phase droplets in an emulsion.

In an embodiment, a composition or compound of the invention is isolated or purified. In an embodiment, an isolated or purified compound is at least partially isolated or purified as would be understood in the art. In an embodiment, the composition or compound of the invention has a chemical purity of 95%, optionally for some applications 99%, optionally for some applications 99.9%, optionally for some applications 99.99%, and optionally for some applications 99.999% pure.

Many of the molecules disclosed herein contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

As used throughout the present description, the expression "a group corresponding to" an indicated species expressly includes a radical (including a monovalent, divalent and trivalent radical) derived from that species.

The compounds of this invention and used with the methods or emulsions of the invention can contain one or more chiral centers. Accordingly, this invention is intended to include racemic mixtures, diastereomers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "substituted" refers to a compound wherein a hydrogen is replaced by another functional group.

As is customary and well known in the art, hydrogen atoms in formulas (FX1)-(FX13) are not always explicitly shown, for example, hydrogen atoms bonded to the carbon atoms of aromatic, heteroaromatic, and alicyclic rings are not always explicitly shown in formulas (FX1)-(FX13). The structures provided herein, for example in the context of the description of formulas (FX1)-(FX13), are intended to convey to one of reasonable skill in the art the chemical composition of compounds of the methods and compositions of the invention, and as will be understood by one of skill in the art, the structures provided do not indicate the specific positions of atoms and bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as attaching and/or spacer groups. Compounds of the invention may have substituted and/or unsubstituted $C_1$-$C_{20}$ alkylene, $C_1$-$C_{10}$ alkylene and $C_1$-$C_5$ alkylene groups.

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as attaching and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups.

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as attaching and/or spacer groups. Compounds of the invention include substituted and/or unsubstituted $C_2$-$C_{20}$ alkenylene, $C_2$-$C_{10}$ alkenylene and $C_2$-$C_5$ alkenylene groups.

As used herein, the terms "cylcoalkenylene" and "cylcoalkenylene group" are used synonymously and refer to a divalent group derived from a cycloalkenyl group as defined herein. The invention includes compounds having one or more cylcoalkenylene groups. Cycloalkenylene groups in some compounds function as attaching and/or spacer groups. Compounds of the invention include substituted and/or unsubstituted $C_3$-$C_{20}$ cylcoalkenylene, $C_3$-$C_{10}$ cylcoalkenylene and $C_3$-$C_5$ cylcoalkenylene groups.

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as attaching and/or spacer groups. Compounds of the invention include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-di hydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, threonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alkyl group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alkyl portion of the groups is substituted as provided herein in connection with the description of alkyl groups. As used herein MeO— refers to $CH_3O$—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6- or 7-member aromatic rings, including heterocyclic aromatic rings. The term heteroaryl specifically refers to aryl groups having at least one 5-, 6- or 7-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine; pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted; and

—NO$_2$.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible. In addition, the compounds of this invention include all stereochemical isomers arising from the substitution of these compounds.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, -32-cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicylic, stearic, succinic, sulfamic, sulfanilic, sulfonic, sulfuric, tannic, tartaric, teoclic, toluenesulfonic, and the like. Pharmaceutically acceptable salts may be derived from amino acids, including but not limited to cysteine. Other pharmaceutically acceptable salts may be found, for example, in Stahl et al., Handbook of Pharmaceutical Salts: Properties, Selection, and Use, Wiley-VCH; Verlag Helvetica Chimica Acta, Zürich, 2002. (ISBN 3-906390-26-8). Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$_4^+$) and substituted ammonium (N(R')$_4^+$, where R is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

The compounds of this invention can contain one or more chiral centers. Accordingly, this invention is intended to include racemic mixtures, diastereomers, enantiomers, tautomers and mixtures enriched in one or more stereoisomer. The scope of the invention as described and claimed encompasses the racemic forms of the compounds as well as the individual enantiomers and non-racemic mixtures thereof.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Supramolecular structure" refers to structures comprising an assembly of molecules. Supramolecular structures include assemblies of molecules, such as linear block copolymers having hydrophilic, hydrophobic and fluorophilic blocks, which are selectively oriented such that hydrophilic portions of the molecules are oriented outward toward a continuous aqueous phase, hydrophobic portions form an inner shell and fluorophilic portions of the molecules are oriented inward to form a fluorous core. Supramolecular structures include assemblies of molecules, such as linear block copolymers having hydrophilic, hydrophobic and fluorophilic blocks, which are selectively oriented such that hydrophilic portions of the molecules are oriented outward toward a continuous aqueous phase, and branched fluorophilic and hydrophobic portions are oriented inward to form a fluorophilic core and intermediate hydrophobic shell. Supramolecular structures include, but are not limited to, micelles, vesicles, tubular micelles, cylindrical micelles, bilayers, folded sheets structures, globular aggregates, swollen micelles, and encapsulated droplets. Supramolecular structures of the present invention include self-assembled structures. Supramolecular structures may comprise the dispersed phase of a colloid, such as an emulsion or nanoemulsion.

"Semi-fluorinated" refers to chemical compounds having at least one fluorine atom, for example molecules having at least one carbon-fluorine bond.

Fluorocarbons as used herein refer to chemical compounds that contain at least one carbon-fluorine bond.

"Perfluorinated" and "perfluorocarbon" refers to chemical compounds that are analogs of hydrocarbons wherein all hydrogen atoms in the hydrocarbon are replaced with fluorine atoms. Perfluorinated molecules can also contain a number of other atoms, including bromine, chlorine, and oxygen. A bromine substituted perfluorocarbon is a perfluorocarbon wherein one or more of the fluorine atoms have been replaced with a bromine atom. A chlorine substituted perfluorocarbon is a perfluorocarbon wherein one or more of the fluorine atoms have been replaced with a chlorine atom. A chlorine and bromine substituted perfluorocarbon is a perfluorocarbon wherein one or more of the fluorine atoms have been replaced with a chlorine atom and wherein one or more of the fluorine atoms have been replaced with a bromine atom.

"Emulsion" refers to a mixture of two or more immiscible substances, such as a mixture of two immiscible liquids. Emulsions are a type of colloid that comprise at least one dispersed phase dispersed in a continuous phase. Emulsions are broadly defined as two immiscible phases in which a first phase is dispersed within a second phase, such as a two-phase system in which one liquid is dispersed throughout a second liquid in the form of small droplets. This energy can either be supplied by mechanical equipment or the chemical potential inherent within the components. The two phases of an emulsion are generally referred to as the continuous phase and the dispersed phase, with the dispersed phase typically present as a smaller volume percentage. A dispersion of oil in water is referred to as an oil-in-water (o/w) emulsion. For o/w emulsions the emulsifying agent is typically more soluble in the aqueous phase. The reverse emulsion, water-in-oil, is abbreviated w/o and is stabilized by surfactants that are more stable in the oil phase. In an aqueous emulsion, the continuous phase is an aqueous solution.

Emulsions are not thermodynamically stable, but the stability can be improved by additives such as surfactants. As non-equilibrium systems, the formation of nanoemulsions generally requires an input of energy. High-energy emulsification methods commonly involve the introduction of mechanical shear through such equipment as high-shear stirrers, high-pressure homogenizers, microfluidizers or ultrasound generators. A microfluidizer is the piece of equipment used in the pharmaceutical industry for the production of emulsions that works by dividing a stream of liquid into two parts, passing each through a narrow opening and then colliding the streams under high pressure. The high shear forces created by the collision provide very fine emulsions with generally narrow particle size distributions. In typical usage, a coarse emulsion (diameter >1 μm) is first formed by some other method, and the size of that larger emulsion is reduced in the microfluidizer. The final droplet size and distribution shape will be dependent upon both the emulsion components (surfactant amount, oil volume percent, etc.) and the processing parameters (time, temperature, pressure etc.). As the desired droplet size decreases, the energy required for formation increases. Ultrasonic emulsification is also effective to reduce the size of emulsion droplets into the nanoscale. Emulsions can also be formed by changing the temperature of a mixture of immiscible liquids, for example by rapid cooling or heating to produce kinetically stable emulsions with small droplet sizes and narrow size distributions.

Emulsions include nanoemulsions comprising nanoscale droplets of one immiscible liquid dispersed within another. As used herein a nanoemulsion is a heterogeneous system composed of one immiscible liquid dispersed as droplets within another liquid, where the average droplet diameter is below 1000 nm.

"Flocculation" refers to a process in which clusters of two or more droplets behave kinetically as a unit, but individual droplets still maintain their identity. Flocculation may be reversible, or lead to coalescence, which is irreversible.

"Coalescence" is the collision, and subsequent irreversible fusion, of two droplets. The ultimate end of coalescence is complete phase separation. Flocculation precedes coalescence, so the same methods that are appropriate for prevention of flocculation also prevent coalescence. A thick, surfactant film adsorbed at the interface is often sufficient to prevent coalescence, whether in nano- or macro-emulsions.

"Ostwald ripening" refers to the growth in the size of emulsion droplets as the contents of one drop diffuse into another. The driving force for this growth is the difference in chemical potential between droplets, which is generally not substantial for droplets larger than 1 μm. Therefore, Ostwald ripening primarily affects nanoemulsions, and is an important factor for nanoemulsions for therapeutic applications.

"Polymer" refers to a molecule comprising a plurality of repeating chemical groups, typically referred to as monomers. A "copolymer", also commonly referred to as a heteropolymer, is a polymer formed when two or more different types of monomers are linked in the same polymer. "Block copolymers" are a type of copolymer comprising blocks or spatially segregated domains, wherein different domains comprise different polymerized monomers. In a block copolymer, adjacent blocks are constitutionally different, i.e. adjacent blocks comprise constitutional units derived from different species of monomer or from the same species of monomer but with a different composition or sequence distribution of constitutional units. Different blocks (or domains) of a block copolymer may reside on different ends of a polymer (e.g. [A][B]), or may be provided in a selected sequence ([A][B][A][B]). "Diblock copolymer" refers to block copolymers having two different chemical blocks. "Triblock copolymer" refers to block copolymers having three different chemical blocks. Polymers of the present invention include block copolymers having a first block comprising a smaller polymer (e.g., 2 to 30 monomers), such as a fluorocarbon, including but not limited to, a fluorocarbon such as a fluorinated or perfluorinated alkane, a second interior hydrophobic block, and a third block comprising a larger polymer (e.g., 10-300) such as a PEG polymer having 10 to 270 monomers. Polymers of the present invention include branched block copolymers comprising a hydrophilic block connected to both a hydrophobic block and a fluorophilic block provided in a branched configuration. Block copolymers of the present invention are capable of undergoing self-assembly to make supramolecular structures, such as encapsulated droplets. As used herein, the term block copolymer includes compositions comprising a first block comprising a PEG polymer conjugated to a second block comprising a hydrophobic polymer and further conjugated to a third block comprising a perfluorinated or semifluorinated molecular domain, such as a perfluorinated or semifluorinated alkane or a perfluorinated or semifluorinated tail. As used herein, the term block copolymer also includes functionalized block copolymers, such as copolymers having additional moieties for targeting a supramolecular structure to an active site, for stabilizing a supramolecular structure or for selecting the release kinetics of a supramolecular structure containing a fluorinated therapeutic compound.

As used herein "hydrophilic" refers to molecules and/or components (e.g., functional groups, blocks of block polymers, etc.) of molecules having at least one hydrophilic group, and hydrophobic refers to molecules and/or components (e.g., functional groups of polymers, and blocks of block copolymers etc.) of molecules having at least one hydrophobic group. Hydrophilic molecules or components thereof tend to have ionic and/or polar groups, and hydrophobic molecules or components thereof tend to have nonionic and/or nonpolar groups. Hydrophilic molecules or components thereof tend to participate in stabilizing interactions with an aqueous solution, including hydrogen bonding and dipole-dipole interactions. Hydrophobic molecules or components tend not to participate in stabilizing interactions with an aqueous solution and, thus often cluster together in an aqueous solution to achieve a more stable thermodynamic state. In the context of block copolymers of the present invention, a hydrophilic block is more hydrophilic than a hydrophobic group of an amphiphilic block copolymer, and a hydrophobic group is more hydrophobic than a hydrophilic block of an amphiphilic polymer.

As used herein "fluorophilic" refers to molecules and/or components (e.g., functional groups, blocks of block polymers etc.) of molecules having at least one fluorophilic group. A fluorophilic group is one that is capable of participating in stabilizing interactions with a fluorous phase. Fluorophilic groups useful in block copolymers of the present invention include, but are not limited to, fluorocarbon groups, perfluorinated groups and semifluorinated groups.

In the context of the present invention the term patient is intended to include a subject such as an animal. Patient includes a mammal, for example human subject. Patient includes a subject undergoing a medical procedure, such as undergoing the administration of anesthesia or other medical procedure.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

Figure 1B:
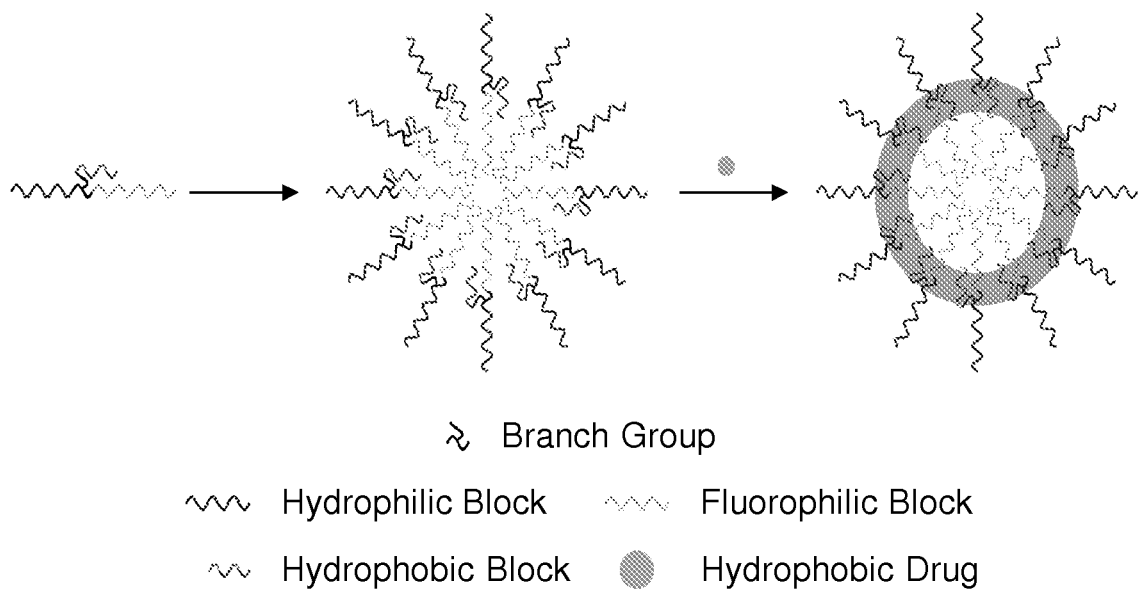
FIG. 1B provides a schematic illustration of the formation of dispersed phase droplets in an emulsion.

FIG. 1A provides a schematic illustration of the formation a supramolecular structure in an emulsion comprising a hydrophobic drug and semi-fluorinated block copolymers comprising a hydrophilic block, a hydrophobic block and a fluorophilic block, optionally including a phospholipid stabilizer component. FIG. 1B, similarly provides a schematic illustration of the formation of a supramolecular structure in an emulsion in which the semi-fluorinated block copolymers have a branched structure comprising a hydrophilic block branch, a hydrophobic block branch and a fluorophilic block branch. As will be understood by one of skill in the art FIGS. 1A and 1B are merely schematic representations to convey an understanding of the components of the present emulsions, and are not intended to provide the actual structures, physical dimensions and relative arrangement of the components of the dispersed droplet phase.

In embodiments, the illustrated configurations are stabilized by self-assembly of the hydrophilic blocks of the semi-fluorinated block copolymers in a configuration so as to associatively interact with the aqueous solution, while simultaneously positioning the fluorophilic and hydrophobic blocks in a configuration toward the interior of the droplet. In some embodiments, for example, the fluorophilic blocks of the semifluorinated block copolymers align to form a fluorous core. In some embodiments, for example, the hydrophobic drug is noncovalently associated with the intermediate shell region of the hydrophobic block of the semi-fluorinated block copolymers. Inclusion of a phospholipid surfactant optionally further stabilizes the droplets and provides more stable emulsions. These configurations advantageously provide a technique for formulation of the hydrophobic drug in the aqueous solution, such that the hydrophobic drug can be administered intravenously to a patient in an aqueous solution based emulsion.

In embodiments, the supramolecular structure is formed with an external facing hydrophilic shell. In embodiments, the supramolecular structure is formed with an intermediate hydrophobic shell. In embodiments, the supramolecular structure is formed with a fluorophilic core. In embodiments, the supramolecular structure is formed with a combination of an external facing hydrophilic shell, an intermediate hydrophobic shell and a fluorophilic core. In some embodiments, the hydrophobic drug accumulates in the supramolecular structure at a region corresponding to an intermediate hydrophobic shell.

The invention may be further understood by the following non-limiting examples.

Example 1: Emulsion-Based Formulations of Propofol

This example provides a description of compositions and physical properties of specific examples of emulsions useful in the present formulations and therapeutic methods. In addition, the results of animal models experiments are provided demonstrating clinical efficacy for examples of the present formulations and therapeutic methods. The description and experimental results are divided into two analysis sections (Analysis Section No. 1 and Analysis Section No. 2) which taken together demonstrate useful properties and applications of certain embodiments of the present invention.

Analysis Section No. 1

Commercial propofol (Diprivan) consists of an Intralipid® emulsion of the active principle 2,6-diisopropylphenol. This emulsion is used extensively in anesthesiology practice to induce and maintain general anesthesia. Propofol is also used for procedural sedation (e.g. colonoscopy) and for sedation in intensive care units.

The current formulation of propofol is subject to a variety of problems, one of the most important being the ability to support bacterial and fungal growth. This is due to the main ingredient of Intralipid®: soybean oil or a similar lipid. Because of the risk of contamination, tubing and open vials of propofol must be replaced every twelve hours. In addition, infusion at a high rate or as a large bolus can lead to lipid intolerance, and may contribute to 'propofol infusion syndrome, a rare but serious complication that limits its use in the intensive care unit. The development of a non-lipidic propofol emulsion would address these problems and thus would be an important advance.

The present example demonstrates the ability of semifluorinated surfactants to stabilize emulsions of various chemicals. For example, we have identified several triblock copolymers that are able to form a stable propofol emulsion without the addition of any lipid component. In certain embodiments, the only additive used is a small percentage of a natural phospholipid Lipoid 80, as found in egg yolk. Several of the emulsions have been studied in rats and shown to be as effective as commercial propofol emulsions in inducing loss of consciousness.

The polymers evaluated comprise a PEG moiety to ensure water solubility, a hydrophobic block, typically a decyl group to complex the propofol, and a medium-sized fluorous group for enhancing the emulsion stability. Different polymer architectures have been tested and all of them are remarkably effective, although with some differences. For instance, addition of a phospholipid to a formulation containing a linear triblock copolymer is useful for generating stable emulsions with propofol. In addition, a PEG-based dibranched polymer in which the fluorous group occupies one branch and the hydrophobic group a second branch, form a stable propofol emulsion, even in the absence of any additive, such as a phospholipid. The stability of this emulsion based on a branched semifluorinated polymer was extended by the addition of a small amount of phospholipid surfactant.

The emulsions described in this example are much simpler in composition than the current commercial propofol and offer the advantage that they do not support microbial growth. In the new emulsions, simple saline can be used to ensure isotonicity instead of glycerol, a chemical required for Intralipid® stability. Importantly, the new emulsions are as effective as the currently used propofol.

Emulsion with Linear Semifluorinated Triblock Copolymer and Phospholipid

The physical properties of propofol emulsions comprising the linear semifluorinated triblock copolymer (M1H10-O—F3) and phospholipid surfactant (E80) were characterized.

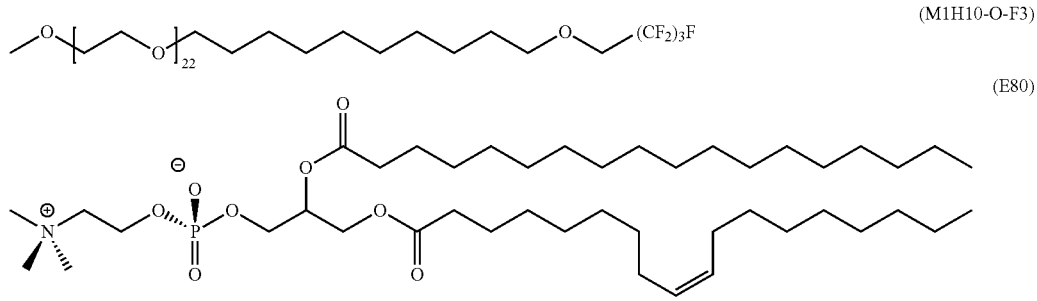

Specifically, the following formulations were evaluated.
Formulation 1:
16.82 mL saline, 420.5 mg M1H10-O—F3 (25 mg/mL), 0.18 mL propofol.
Formulation 2:
16.82 mL saline, 420.5 mg M1H10-O—F3 (25 mg/mL), 100.9 g E80 (6 mg/mL), 0.18 mL propofol.
Formulation 3:
16.82 mL saline, 420.5 mg M1H10-O—F3 (25 mg/mL), 151.4 g E80 (9 mg/mL), 0.18 mL propofol.
Formulation 4:
16.82 mL saline, 420.5 mg M1H10-O—F3 (25 mg/mL), 201.8 g E80 (12 mg/mL), 0.18 mL propofol.

Figure 2:
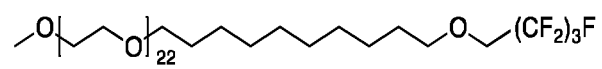
FIG. 2. provides a plot showing the mean droplet diameter (nm) for emulsions corresponding to formulations 1-4 evaluated as a function of time (days).
Figure 2:
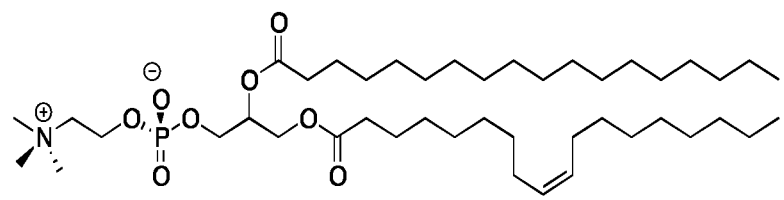
Figure 2:
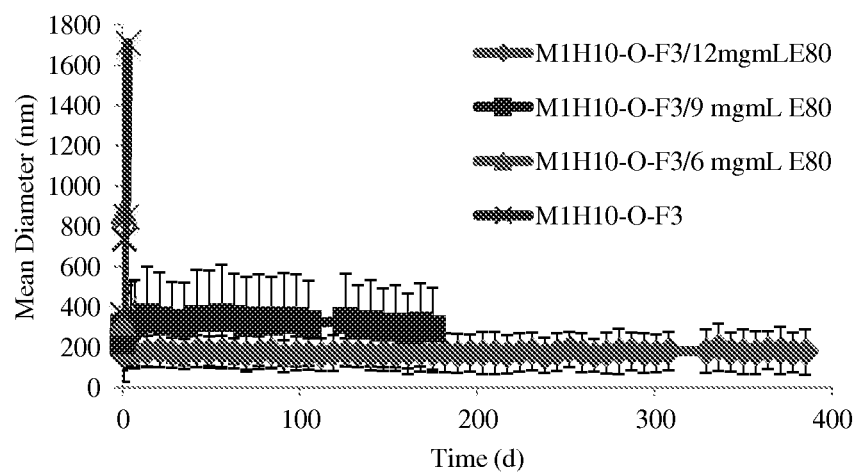

FIG. 2 provides a plot showing the mean droplet diameter (nm) for emulsions corresponding to formulations 1-4 evaluated as a function of time (days). As shown in FIG. 2, formulations 1 and 2 were observed to undergo rapid droplet growth upon emulsification. In contrast, formulations 3 and 4 corresponding to higher concentrations of the phospholipid surfactant (E80) formed stable emulsions with mean droplet diameters of about 300 nm and 200 nm, respectively, that did not undergo appreciable change in droplet size over a period of several months.

The physical properties of propofol emulsions comprising the linear semifluorinated triblock copolymer (M1H10-O—F6) and phospholipid surfactant (E80) were characterized.

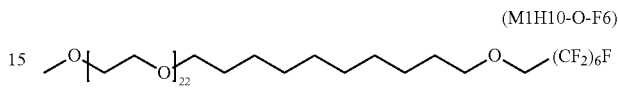

Specifically, the following formulations were evaluated.
Formulation 5:
16.82 mL MiliQ, 420.5 mg M1H10-O—F3 (25 mg/mL), 201.8 g E80 (12 mg/mL), 0.18 mL propofol
Formulation 6:
16.82 mL saline, 420.5 mg M1H10-O—F3 (25 mg/mL), 201.8 g E80 (12 mg/mL), 0.18 mL propofol.

Figure 4:
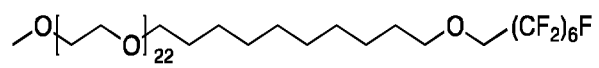
FIG. 4. provides a plot showing the mean droplet diameter (nm) for the emulsions corresponding to formulations 5 and 6 corresponding to MiliQ and saline aqueous phases, respectively, as a function of time (days).
Figure 4:
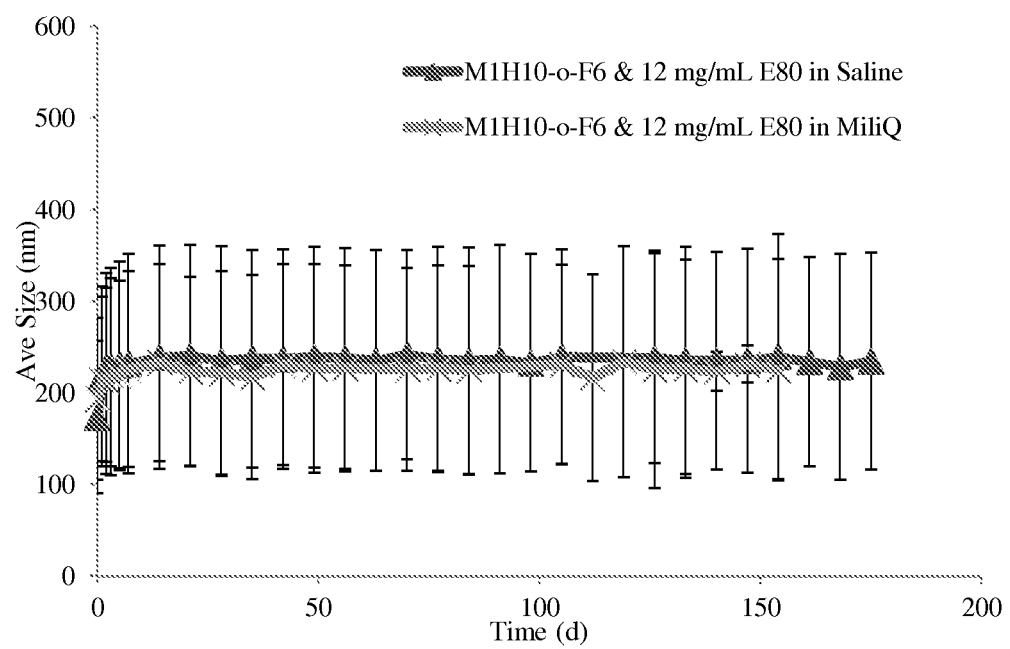

FIG. 4 provides a plot showing the mean droplet diameter (nm) for the emulsions corresponding to formulations 5 and 6 corresponding to MiliQ and saline aqueous phases, respectively, as a function of time (days). As shown in FIG. 4, formulations 5 and 6 formed stable emulsions with mean droplet diameters of about 225 nm that did not undergo appreciable change in droplet size over a period of several months. The results demonstrate the present emulsions are compatible with formulation using saline solution, which has particular relevance for clinic use.

Emulsions with Branched Semifluorinated Triblock Copolymers

The physical properties of a propofol emulsion comprising the branched semifluorinated triblock copolymer (M1μH10F8) without a phospholipid surfactant were characterized.

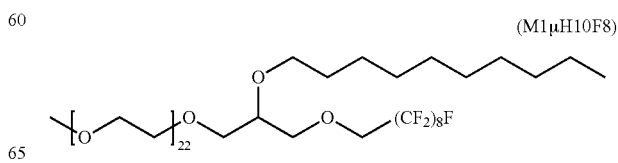

Specifically, the following formulation was evaluated.
Formulation 7:

16.82 mL saline, 420.5 mg (25 mg/ml) M1μH10F8, 0.18 mL propofol.

Figure 3:
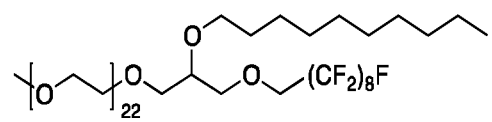
FIG. 3. provides a plot showing the mean droplet diameter (nm) for the emulsion corresponding to formulation 7 evaluated as a function of time (days).
Figure 3:
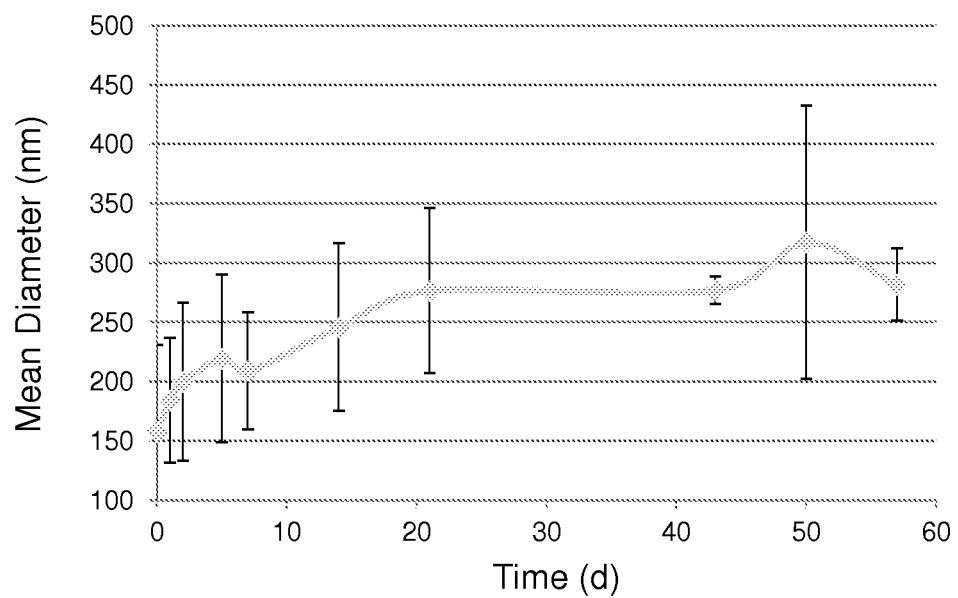

FIG. 3 provides a plot showing the mean droplet diameter (nm) for the emulsion corresponding to formulation 7 evaluated as a function of time (days). As shown in FIG. 3, formulation 7 formed a stable emulsion wherein the mean droplet diameter was observed to increase from an initial value of about 150 nm to about 300 nm over a period of about two months.

The physical properties of a propofol emulsion comprising the branched semifluorinated triblock copolymer (M2μH18F8) without a phospholipid surfactant were characterized.

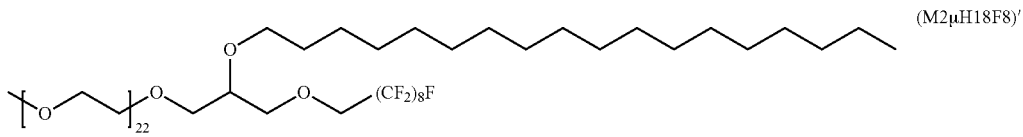

(M2μH18F8)'

Specifically, the following formulation was evaluated.
Formulation 8:

16.82 mL saline, 420.5 mg (25 mg/ml) M2μH18F8, 0.18 mL propofol.

Figure 5:
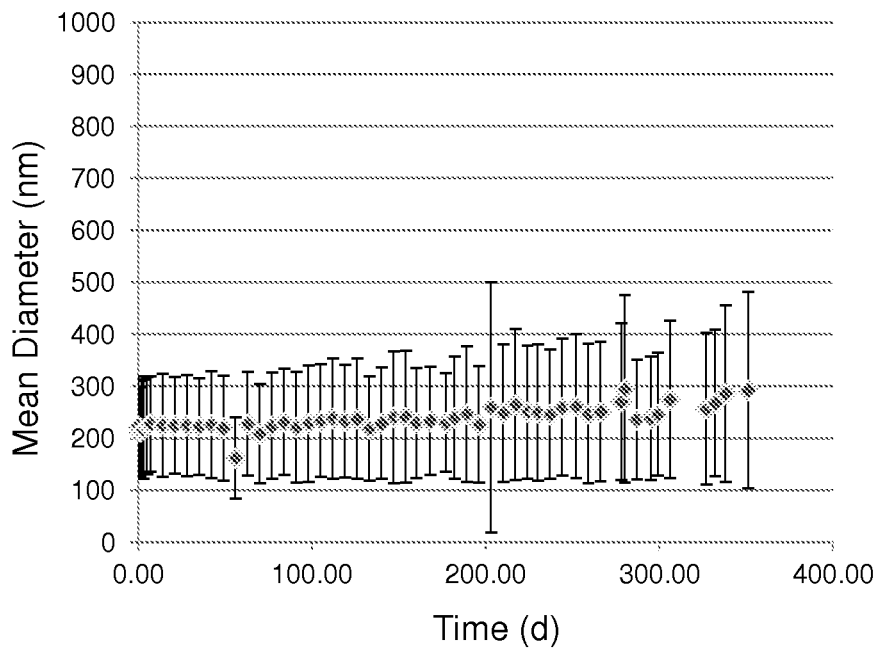
FIG. 5. provides a plot showing the mean droplet diameter (nm) for the emulsion corresponding to formulation 8 evaluated as a function of time (days).

FIG. 5 provides a plot showing the mean droplet diameter (nm) for the emulsion corresponding to formulation 8 evaluated as a function of time (days). As shown in FIG. 5, formulation 8 formed a stable emulsion wherein the mean droplet diameter was observed to increase from an initial value of about 200 nm to about 300 nm over a period of about two months.

Unstable Emulsions

A number of formulations were evaluated that resulted in formation of an unstable propofol emulsion.

The physical properties of a propofol emulsion comprising the branched block copolymer (M5diH10) were characterized.

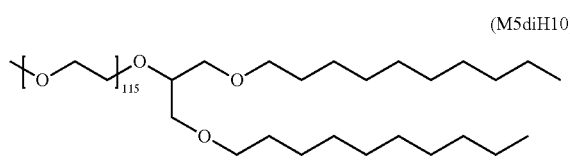

(M5diH10)

Specifically, the following formulation was evaluated.
Formulation 9:

16.82 mL normal saline with 420.5 mg M5diH10 and 0.18 mL propofol

Figure 6:
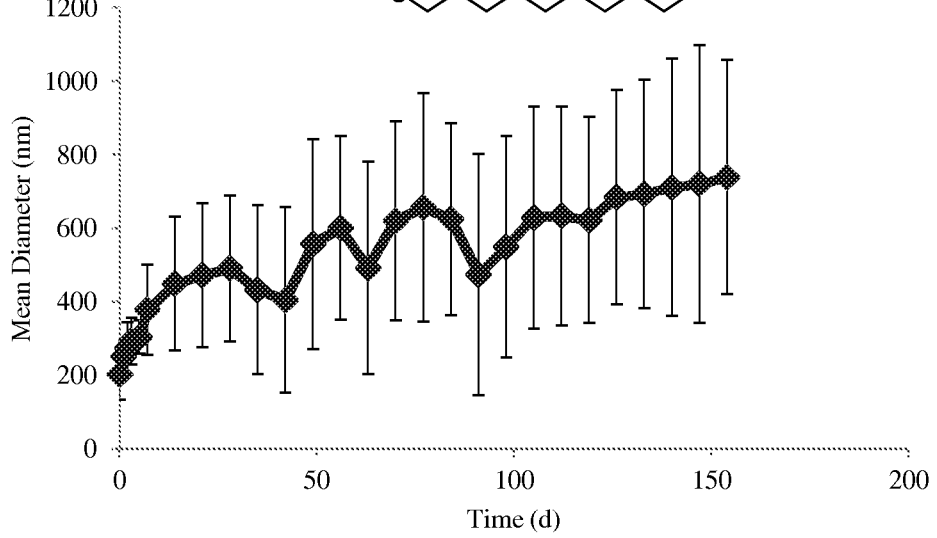
FIG. 6. provides a plot showing the mean droplet diameter (nm) for the emulsion corresponding to formulation 9 evaluated as a function of time (days).

FIG. 6 provides a plot showing the mean droplet diameter (nm) for the emulsion corresponding to formulation 9 evaluated as a function of time (days). As shown in FIG. 6, formulation 9 did not form a stable emulsion wherein the mean droplet diameter was observed to increase from an initial value of about 200 nm to about 700 nm over a period of several months.

The physical properties of emulsions comprising the diblock copolymer (M1H10) with and without the phospholipid surfactant (E80) were characterized.

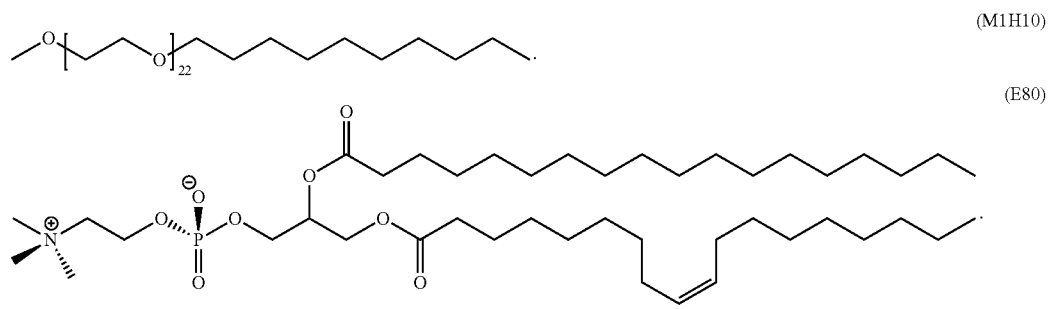

(M1H10)

(E80)

Specifically, the following formulations were evaluated.
Formulation 10:

16.82 mL saline, 420.5 mg M1H10, 0.18 mL propofol

Formulation 11:

16.82 mL saline, 420.5 mg M1H10, 201.8 mg E80, 0.18 mL propofol

Figure 7:
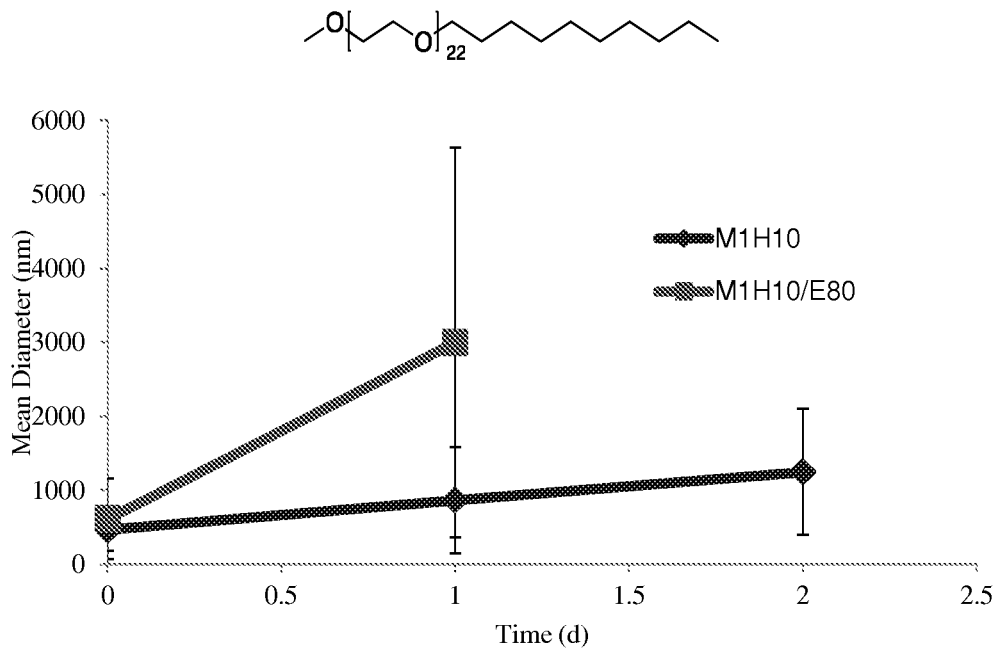
FIG. 7. provides a plot showing the mean droplet diameter (nm) for the emulsions corresponding to formulations 10 and 11 evaluated as a function of time (days).

FIG. 7 provides a plot showing the mean droplet diameter (nm) for the emulsions corresponding to formulations 10 and 11 evaluated as a function of time (days). As shown in FIG. 7, formulations 10 and 11 did not form stable emulsions as the mean droplet diameter was observed to increase from an initial value of about 500 nm to about 2800 nm (formulation 10) and 1000 nm (formulation 11) over a period of one to two days.

The physical properties of propofol emulsions comprising a phospholipid surfactant (E80) were evaluated for saline and MiliQ aqueous phases.

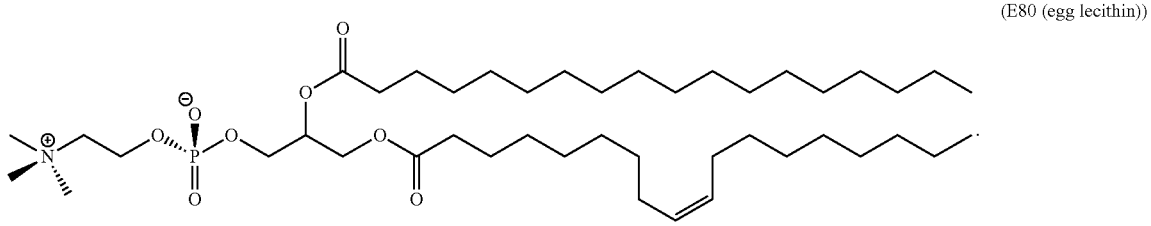
(E80 (egg lecithin))

Figure 8:
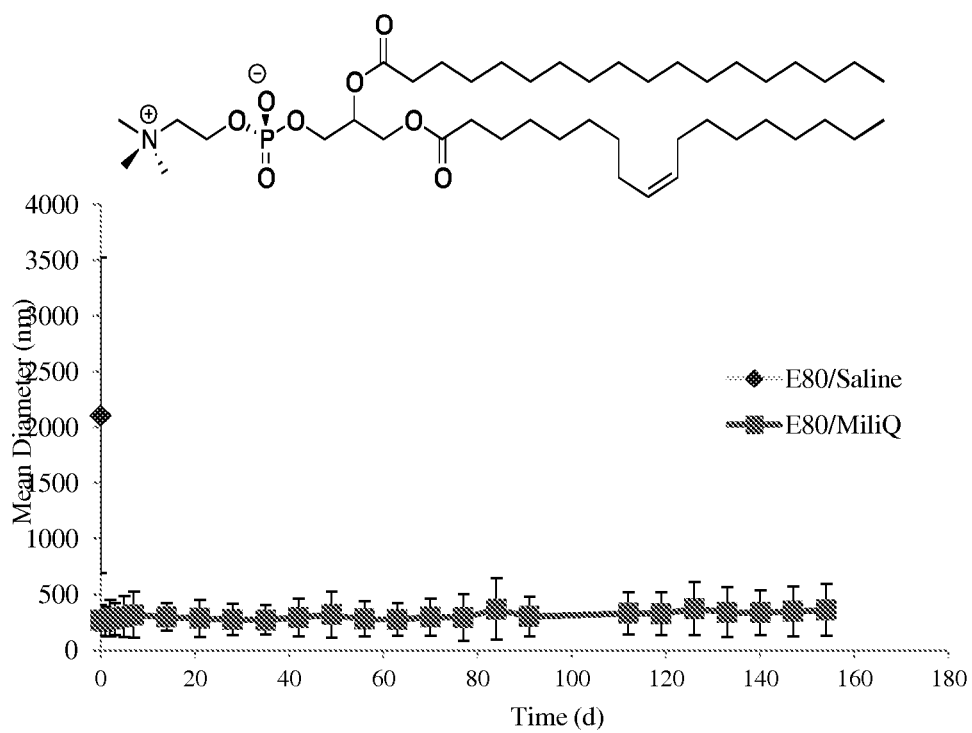
FIG. 8. provides a plot showing the mean droplet diameter (nm) for the emulsions corresponding to formulations 12 and 13 evaluated as a function of time (days).

Specifically, the following formulations were evaluated.
Formulation 12 (in Saline):
 16.82 mL saline, 201.8 g E80, 0.18 mL Propofol
Formulation 13 (in MiliQ):
 16.82 mL MiliQ, 201.8 g E80, 0.18 mL Propofol FIG. 8 provides a plot showing the mean droplet diameter (nm) for the emulsions corresponding to formulations 12 and 13 were evaluated as a function of time (days). As shown in FIG. 8, formulation 12 did not form a stable emulsion and formulation 13 formed a stable emulsion characterized by a mean diameter of about 300 nm that did not change appreciably for a period of several months. These experimental results demonstrate that phospholipid surfactant (E80) does not form a stable emulsion with a continuous phase comprising a saline solution.

Animal Studies

Figure 9:
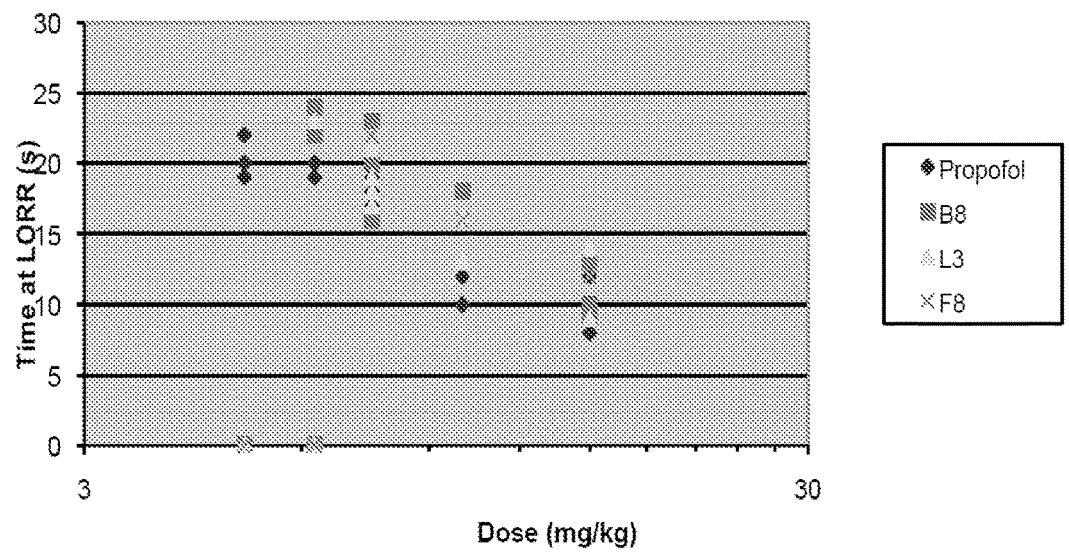
FIG. 9. provides plots of time to Loss of Righting Reflex (LORR) (s) as a function of dose (mg/kg).
Figure 10:
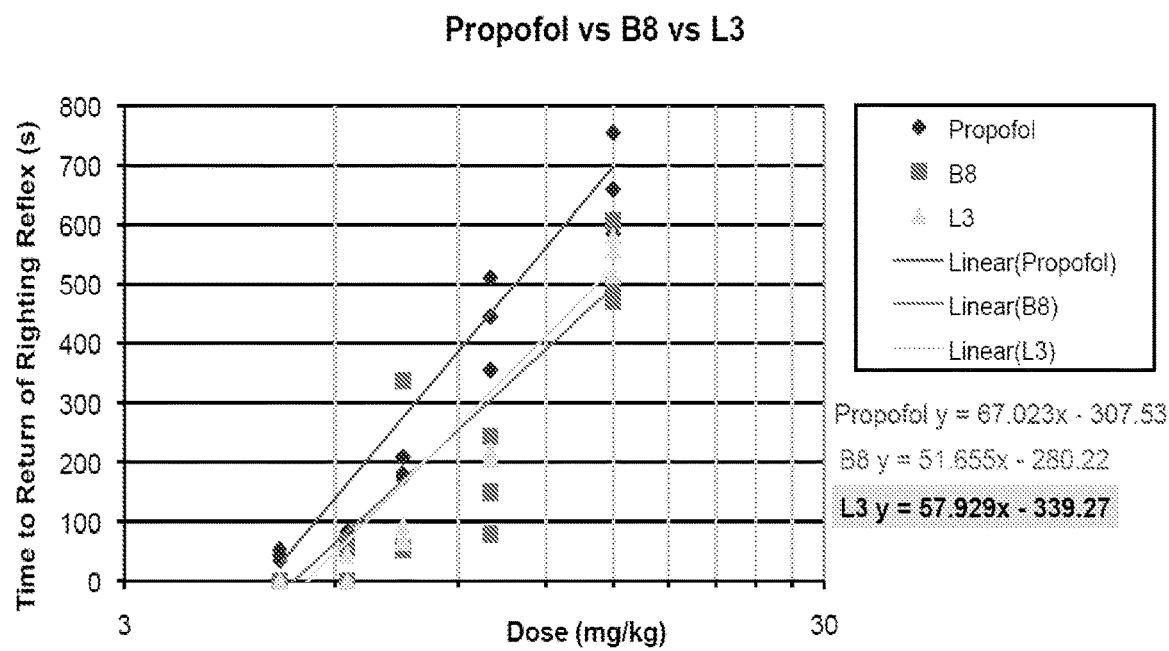
FIG. 10. provides plots of time to Time to Return of Righting Reflex (s) as a function of dose (mg/kg).

FIGS. 9 and 10 show the results of animal studies for the administration of propofol emulsions. All animal studies were approved by the University of Wisconsin Animal Care and Use Committee, Madison, Wis., and were performed in accordance with the guidelines laid out in the Guide for the Care and Use of Laboratory Animals published by the National Research Council.

Experiments to measure loss and recovery of the righting reflex were carried out in six male Spraque-Dawley rats (Harlan Spraque-Dawley, Inc., Indianapolis, Ind.) weighing approximately 280 g. The rats were received from the supplier with a surgically implanted jugular catheter. Different propofol formulations were tested: 1) lipid-based propofol formulation as in current clinical use (Propofol: Diamonds); 2) Formulation 7 (B8; Squares; 16.82 mL saline, 420.5 mg (25 mg/ml) M1μH10F8, 0.18 mL propofol); 3) Formulation 4 (L3; Triangles, 16.82 mL saline, 420.5 mg M1H10-O—F3 (25 mg/mL), 201.8 g E80 (12 mg/mL), 0.18 mL propofol) and 4) Formulation 14 (F8: Xs: 13.42 mL saline, 280 mg M1H10F8, 0.18 mL propofol, 3.4 mL PFOB). For each formulation, five different doses were administered three times each.

The propofol emulsions were administered by first restraining the rat with a towel. The plug placed at the end of the catheter was then removed and replaced with a 23-gauge needle connected to an insulin-type syringe. To remove the heparin-based fill solution and check that no blockage was obstructing the catheter, the syringe plunger was slowly withdrawn until blood filled the catheter. The 23-gauge needle was then connected to the syringe containing the propofol emulsion to be tested. The rat was then placed in a transparent cage for observation. Forty μL of the emulsion, corresponding to the volume of the catheter, was injected to prime the catheter and then the administration of the emulsion was started. The emulsion injection rate was controlled through an infusion pump (11 plus; Harvard Apparatus, Holliston, Mass.). A bolus dose was delivered within 20 s regardless of the volume. Loss of righting reflex (LORR) was evaluated by rolling the rat onto its back and observing whether the animal was able to right itself. The times to achieve and to recover from LORR were recorded. When the rat completely recovered from LORR, the catheter was flushed with 0.04 ml of a normal saline solution to remove the residual emulsion and then refilled with 0.04 ml of a heparin-based fill solution. The end of the catheter was sealed with a sterile plug.

FIG. 9 provides plots of time to LORR (s) as a function of dose (mg/kg). FIG. 10 provides plots of time to Time to Return of Righting Reflex (s) as a function of dose (mg/kg). Data are plotted as time to loss or recovery of righting reflex as a function of drug dose, expressed on a mg/kg basis for the propofol component of the nanoemulsion. The x-axis intersection is the calculated ED50 for inducing LORR as a surrogate for unconsciousness. All three formulations proved effective with similar ED50 values. The data shown in FIGS. 9 and 10 indicate efficacies of the present emulsions having semifluorinated block copolymer are comparable to the lipid-based propofol formulation currently in use.

Experimental Section

Structures of linear branched, and miktoarm amphiphiles presented in this example with associated nomenclature are shown below.

Linear Amphiphiles

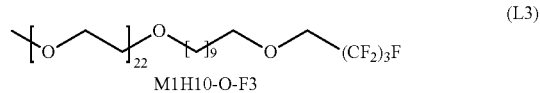
(L3)
M1H10-O-F3

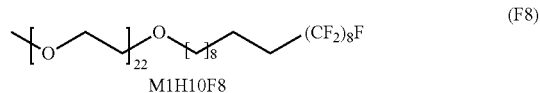
(F8)
M1H10F8

Miktoarm amphiphile

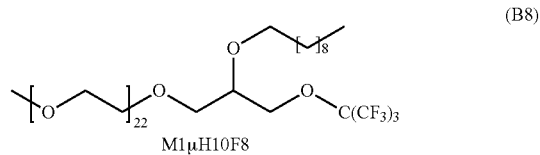
(B8)
M1μH10F8

Mx refers to the mPEG hydrophilic block with x being the average molecular weight in thousands. For non-linear amphiphiles, μ specifies miktoarm architecture, respectively. H# corresponds to the number of hydrogenated carbon atoms and F# corresponds to the number of fluorinated carbon atoms. For the linear polymers, the presence or absence of —O— indicates the presence or absence of an ether linkage between the blocks.

Materials

All fluorinated compounds were obtained from SynQuest Laboratories, Inc. (Alachua, Fla., USA), Lipoid E80 was purchased from Lipoid GmbH (Ludwigshafen, Germany).

All solvents were of ACS grade or higher and were purchased from Sigma-Aldrich (St. Louis, Mo., USA). All other reagents were purchased from Sigma Aldrich (St. Louis, Mo., USA) and were used as received, unless otherwise specified. Chromatographic separations were performed using Silicycle 60 Å SiO$_2$. Surfactants were purified automated flash chromatography using a Combi Flash® Rf 4× system (Teledyne Isco, Lincoln, Nebr., USA) equipped with a Gold C-18 aqueous reverse phase cartridge. $^1$H- and $^{19}$F-NMR spectra were obtained on Varian Unity-Inova 400 and Unity-Inova 500 spectrometers using deuterochloroform (CDCl$_3$) as the solvent with TMS as an internal reference.

Radical Synthesis

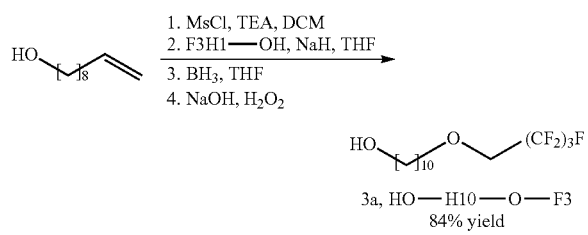

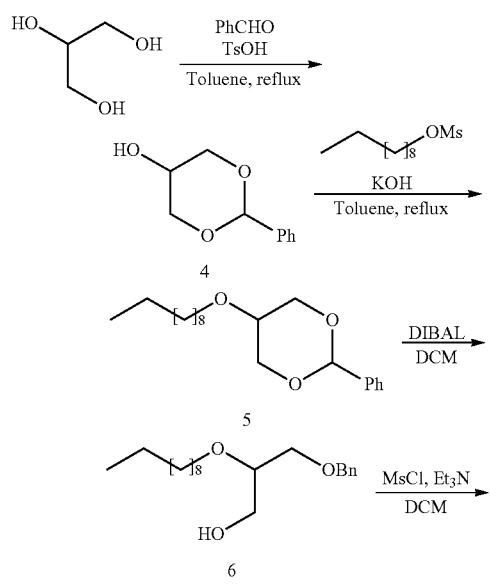

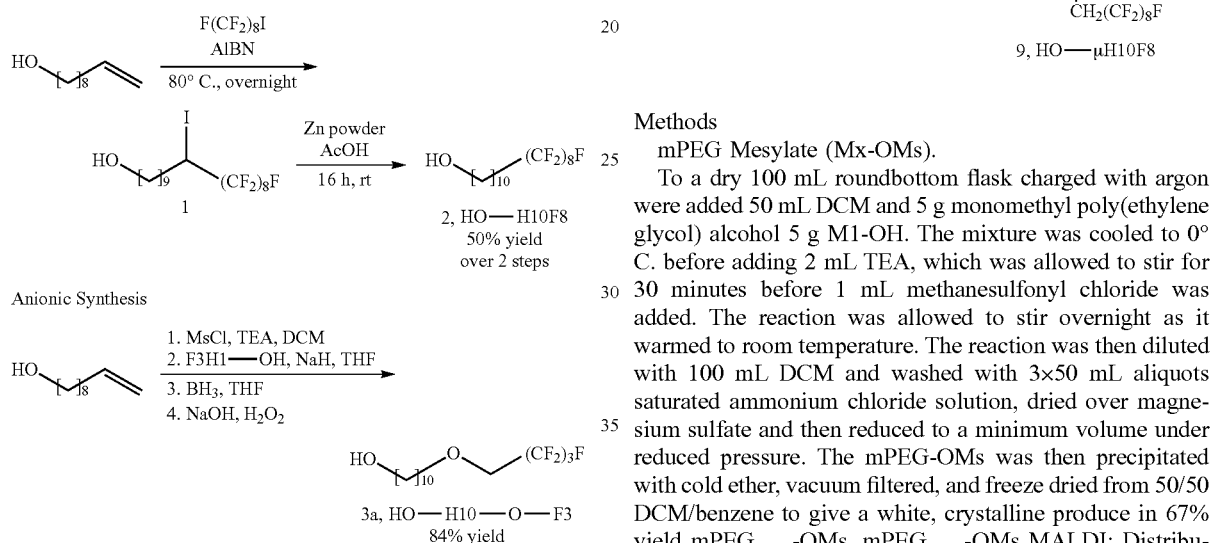

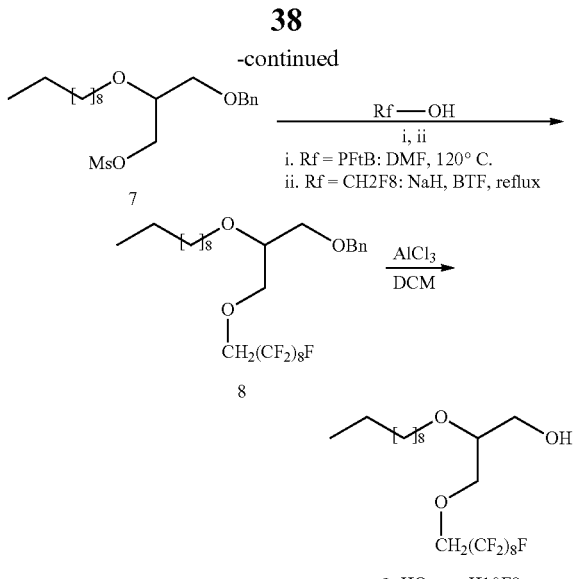

Methods mPEG Mesylate (Mx-OMs).

To a dry 100 mL roundbottom flask charged with argon were added 50 mL DCM and 5 g monomethyl poly(ethylene glycol) alcohol 5 g M1-OH. The mixture was cooled to 0° C. before adding 2 mL TEA, which was allowed to stir for 30 minutes before 1 mL methanesulfonyl chloride was added. The reaction was allowed to stir overnight as it warmed to room temperature. The reaction was then diluted with 100 mL DCM and washed with 3×50 mL aliquots saturated ammonium chloride solution, dried over magnesium sulfate and then reduced to a minimum volume under reduced pressure. The mPEG-OMs was then precipitated with cold ether, vacuum filtered, and freeze dried from 50/50 DCM/benzene to give a white, crystalline produce in 67% yield mPEG$_{1000}$-OMs. mPEG$_{1000}$-OMs MALDI: Distribution centered on [M+Na$^+$]=1063, PDI of starting mPEG 1.27. NMR: $^1$H NMR (400 MHz, CDCl$_3$): δ 4.38 (m, 2H), 3.82 (m, 1H), 3.77 (m, 2H), 3.64 (m, 89H), 3.55 (m, 2H), 3.47 (m, 1H), 3.38 (s, 3H), 3.09 (s, 3H).

Linear Alcohols.

HO—H10F8 (2): To a dry 10 mL roundbottom flask were added 1.02 mL (5.75 mmol) 9-decen-1-ol and 1.34 mL (5.0 mmol) perfluorooctyl iodide. The mixture was degassed at room temperature with argon for 45 minutes before 8.2 mg (0.05 mmol) AIBN were added and the mixture slowly heated to 80° C. while being very rapidly stirred with a small stir bar. This reaction was allowed to run overnight. The reaction was then cooled to room temperature, diluted with 100 mL DCM, washed with 1×50 mL aliquot each Na$_2$S$_2$O$_3$ and brine. The organic layers were dried over MgSO$_4$ and condensed under reduced pressure to give an off-white solid (1). This was then dissolved in 10 mL acetic acid and stirred with 0.98 g zinc powder for 24 hours open to the air. The reaction was then quenched with 200 mL saturated NaHCO$_3$ solution and extracted with 300 mL DCM. The organic layers were then washed with 1×100 mL aliquot each saturated NaHCO$_3$ solution and brine and then dried over MgSO$_4$ and concentrated under reduced pressures to give a white solid. The solid was recrystallized twice from hot toluene to give pure (2) HO—H10F8 in 48% yield. NMR: $^1$H NMR (400 MHz, CDCl$_3$): δ 3.65 (t, J=6.9 Hz, 2H), 2.05 (ttt, J=18, 9.5, 2 Hz, 2H), 1.65-1.52 (m, 4H), 1.4-1.23 (m, 12H). ¹⁹F NMR (376 MHz, CDCl₃): δ −81.15 (3F), −114.77 (2F), −122.32 (6F), −123.11 (2F), −123.92 (2F), −126.49 (2F).

HO—H10-O—F3 (3): To a dry roundbottom, on ice under argon, were added 25 mL dry DCM, 9-decen-1-ol (2.5 mL, 13 mmol) and TEA (4.3 mL, 31 mmol). This was allowed to react for 30 minutes before methanesulfonyl chloride (1.3 mL, 16 mmol) was added dropwise. After running overnight, the reaction was diluted with 50 mL DCM and then washed with 3×50 mL of saturated ammonium chloride solution. The organic layer was then dried over magnesium sulfate and concentrated under reduced pressure to give 3.21 g (quantitative yields) of yellow oil. NMR: ¹H NMR (400 MHz, CDCl₃): δ 5.81 (ddt, J=16.5, 10, 6.5 Hz, 1H), 4.99 (ddt, J=16.5, 2, 1 Hz, 1H), 4.93 (ddt, J=10, 2, 1 Hz, 1H), 4.22 (t, J=7 Hz, 2H), 3.00 (s, 3H), 2.04 (qt, J=6.5, 1 Hz, 2H), 1.60 (q, J=7 Hz, 2H), 1.41-1.29 (m, 10H).

To a 100 mL oven-dried roundbottom, under argon, were added 35 mL of THF and 761 mg of NaH. The suspension was cooled to 0° C. over the course of 10 minutes before 28 mmol of semi-fluorinated alcohol were added 3.25 mL 1H,1H-perfluorobutan-1-ol (F3H1-OH) was added dropwise over the course of 1 hour. Then 3.20 g (13 mmol) of 9-decen-1-yl methane sulfonate were added (as a solution in 10 mL of anhydrous THF). This was then warmed slowly to reflux and allowed to react for 24 hours. The reaction was then allowed to cool and diluted with 100 mL of DCM. This was washed with 3×50 mL aliquots of saturated ammonium chloride solution and then dried over magnesium sulfate and concentrated under reduced pressure to give an opaque, yellow liquid. The product was then purified by column chromatograph (4% ethyl acetate in hexanes) to give 3.83 g (86% yield) and of product as a clear liquid. 10-(1H,1H-perfluorobutoxy)dec-1-ene NMR: ¹H NMR (400 MHz, CDCl₃): δ 5.81 (ddt, J=16.5, 10, 6.5 Hz, 1H), 4.99 (ddt, J=16.5, 2, 1 Hz, 1H), 4.93 (ddt, J=10, 2, 1 Hz, 1H), 3.90 (tt, J=14, 2 Hz, 2H), 3.58 (t, J=7 Hz, 2H), 2.04 (qt, J=6.5, 1 Hz, 2H), 1.60 (q, J=7 Hz, 2H), 1.41-1.29 (m, 10H). ¹⁹F NMR (376 MHz, CDCl₃): δ −81.51 (3F), −121.09 (2F), −128.28 (2F).

To an oven-dried round-bottom flask was added BH₃-THF (1.0M, 16.5 mmol). The solution was diluted with 10 mL of dry THF and then cooled to 0° C. The semi-fluorinated alkene ether 3.83 g 10-(1H,1H-perfluorobutoxy)dec-1-ene was added dropwise and the reaction was allowed to stir at room temperature for 16 h. The reaction was cooled to 10° C. followed by addition of NaOH solution (3M, 20 mL). Hydrogen peroxide (30 wt. % in water, 6 mL) was added at 10° C. The reaction mixture was stirred at 50° C. for 2 h and then cooled to room temperature. Ether (20 mL) was added and the organic phase was washed with H₂O (20 mL), brine (20 mL), dried over magnesium sulfate and concentrated under reduced pressure to give 3.9 g (98% yield) HO—H10-O—F3 (3) of clear oil. HO—H10-O—F3 NMR: ¹H NMR (400 MHz, CDCl₃): δ 3.90 (tt, J=14, 2 Hz, 2H), 3.64 (t, J=7 Hz, 2H), 3.58 (t, J=7 Hz, 2H), 1.60 (septet, J=7 Hz, 4H), 1.41-1.29 (m, 12H). ¹⁹F NMR (376 MHz, CDCl₃): δ −81.51 (3F), −121.08 (2F), −128.28 (2F).

Miktoarm Alcohols.

HO-μF8H10 (9): 5 g decanol was dissolved in anhydrous DCM (50.0 mL) and flask flushed with Ar. 8.80 mL TEA was added to solution and flask cooled in ice bath and 3.70 mL MsCl was then added via syringe, dropwise, and reaction stirred under Ar overnight, allowing the ice bath to warm to room temperature. The reaction was then stopped and washed with 4×100 mL aliquots of aqueous NH₄Cl, dried over MgSO₄ and solvent removed under vacuum. Yield: 7.413 g decyl methane sulfonate (99%). Decyl methane sulfonate: ¹H NMR (400 MHz, CDCl₃): δ 4.22 (t, J=6.6 Hz, 2H), 3.00 (s, 3H), 1.75 (p, J=6.7 Hz, 2H), 1.42 (t, J=7.5 Hz, 2H), 1.26 (m, 12H), 0.88 (t, J=6.8 Hz, 3H).

2-phenyl-1,3-dioxan-5-ol (4): glycerol (24.31 g, 264.0 mmol) and benzaldehyde (28.03 g, 264.1 mmol) were dissolved in anhydrous toluene (70 mL) and flask flushed with argon. P-toluenesulfonic acid monohydrate (115.1 mg, 0.61 mmol) was added and flask fitted with Dean-Stark trap and heated to reflux. After 72 hours, the reaction was cooled to room temperature and washed with sodium bicarbonate (100 mL), brine (100 mL), dried over MgSO₄, and remaining toluene was placed in freezer overnight to crystallize out product. White crystals were then collected by filtration and dried under vacuum to yield 4.487 g (24.90 mmol, 9%). NMR: ¹H NMR (400 MHz, CDCl₃): δ 7.48 (m, 2H), 7.36 (m, 3H), 5.50 (s, 1H), 4.12 (dd, J=12.0, 1.4 Hz, 2H), 4.02 (dd, J=12.0, 1.3 Hz, 2H), 3.54 (dt, J=10.6, 1.5 Hz, 1H), 3.36 (d, J=10.5 Hz, 1H).

5-(decyloxy)-2-phenyl-1,3-dioxane (5): 3.686 g 2-phenyl-1,3-dioxan-5-ol (4) was dissolved in 80 mL anhydrous toluene and 2.30 g crushed added. Reaction fitted with Dean-Stark trap and heated to reflux for 6 hours. The reaction was then cooled, and 7.413 decyl methane added as solution in toluene (20 mL). The reaction was fitted with a condenser and heated to reflux for 5 days. The reaction was then cooled to room temperature, diluted with 100 mL water, extracted with 3×100 mL aliquots of ether, dried over MgSO₄ and solvents removed under reduced pressure. Crude oil purified by flash column (5% ethyl acetate in hexanes) to obtain 3.309 g 5-(decyloxy)-2-phenyl-1,3-dioxane (10.33 mmol, 51%) (5). ¹H NMR (400 MHz, CDCl₃): δ 7.50 (m, 2H), 7.33 (m, 3H), 5.54 (s, 1H), 4.31 (dd, J=12.4, 1.2 Hz, 2H), 4.02 (dd, J=12.4, 1.6 Hz, 2H), 3.53 (t, J=6.8 Hz, 2H), 3.24 (t, J=2.0 Hz, 1H), 1.65 (p, J=6.8 Hz, 2H), 1.28 (m, 14H), 0.88 (t, J=6.8 Hz, 3H).

3-(benzyloxy)-2-(decyloxy)propan-1-ol (6): 7.745 g 5 was dissolved in 50 mL anhydrous DCM and flask flushed with Ar. The reaction was cooled in an ice bath, and 48.3 mL 1 M DIBAL was added dropwise over 20 minutes and the reaction stirred overnight, allowing the reaction to warm to room temperature. The reaction was quenched dropwise with 30 mL 0.5 M, then diluted with 10 mL 0.5 M NaOH and extracted with 2×50 mL aliquots DCM. Combined organics were washed with 2×100 mL aliquots Rochelle's salt, 100 mL brine, dried over MgSO₄ and solvent removed under reduced pressure. Crude oil was purified with silica column (0-5% methanol in DCM) to yield 6.01 g 3-(benzyloxy)-2-(decyloxy)propan-1-ol (6) (77%). ¹H NMR (400 MHz, CDCl₃): δ 7.36-7.26 (m, 5H), 4.54 (AB quartet, 2H), 3.74 (m, 1H), 3.66-3.48 (m, 6H), 2.10 (dd, J=5.7, 6.9 Hz, 1H), 1.57 (p, J=7.0 Hz, 2H), 1.26 (m, 14H), 0.88 (t, J=6.8 Hz, 3H).

3-(benzyloxy)-2-(decyloxy)propyl methanesulfonate (7): 6.01 g of 6 was dissolved in 300 mL anhydrous DCM and flask flushed with Ar. 5.20 mL TEA was added and reaction cooled in ice bath. 2.20 mL MsCl was added dropwise and the reaction was stirred under Ar overnight, allowing ice bath to warm to room temperature. The reaction was then diluted with DCM (50 mL) and washed with 3 aliquots saturated NH₄Cl solution, dried over MgSO₄ and solvents removed under reduced pressure to give a pale yellow oil. 77.102 g (95% yield). 7 ¹H NMR (400 MHz, CDCl₃): δ 7.33 (m, 5H), 4.54 (dd, J=12.1, 2.3 Hz, 2H), 4.39 (dd, J=10.9, 3.8 Hz, 1H), 4.27 (dd, J=10.8, 5.7 Hz, 1H), 3.70 (p, J=4.7 Hz, 1H), 3.55 (m, 4H), 3.00 (s, 3H), 1.56 (p, J=6.8 Hz, 2H), 1.28 (m, 14H), 0.88 (t, J=6.8 Hz, 3H).

((2-(decyloxy)-3-(1H,1Hperfluorononyloxy)propoxy)methyl)benzene (8): 3.160 g 7 was dissolved in anhydrous BTF, and 5.12 g F8H1-OH added, and flask flushed with Ar. 667 mg NaH were slowly added, and reaction heated to reflux for 3 days. Reaction was quenched dropwise with $H_2O$ and further diluted with water and DCM and layers separated. Organics dried over $MgSO_4$ and solvents evaporated under vacuum. Purified by column chromatography (5% ethyl acetate in hexanes) to obtain pure 8 in 67% yield (3.985 g). 8a $^1$H NMR (400 MHz, $CDCl_3$): δ 7.33 (m, 5H), 4.54 (s, 2H), 4.00 (t, J=13.9 Hz, 2H), 3.76 (dd, J=10.4, 4.0 Hz, 1H), 3.68 (dd, J=10.4, 5.6 Hz, 1H), 3.61 (p, J=4.7 Hz, 1H), 3.54 (m, 4H), 1.56 (p, J=6.8 Hz, 2H), 1.28 (m, 14H), 0.88 (t, J=6.8 Hz, 3H). $^{19}$F NMR (376 MHz, $CDCl_3$): δ −81.19 (3F), −120.22 (m, 2F), −122.38 (m, 6F), −123.12 (m, 2F), −123.80 (m, 2F), −126.52 (m, 2F).

HO-μH10F8 (9): 3.679 g 8 was dissolved in 180 mL anhydrous DCM and 2.10 mL anisole was added. Flask was flushed with Ar and cooled in ice bath. 1.951 g $AlCl_3$ was added and reaction was stirred under Ar. After 18 hours reaction was quenched dropwise with 0.5 M HCl, and further diluted with 0.5 M HCl and layers separated. Organic layer was washed with $H_2O$, brine, dried over $MgSO_4$ and solvents were removed under reduced pressure. Crude oil was purified by column chromatography, 10-40% ethyl acetate in hexanes to give pure 2.875 g pure 9 (89% yield). HO-μH10F8 $^1$H NMR (400 MHz, $CDCl_3$): δ 4.00 (t, J=13.7 Hz, 2H), 3.73 (m, 3H), 3.57 (m, 4H), 2.00 (t, J=6.1 Hz, 1H), 1.57 (p, J=7.1 Hz, 2H), 1.26 (m, 14H), 0.88 (t, J=6.8 Hz, 3H). $^{19}$F NMR (376 MHz, $CDCl_3$): δ −81.25 (t, J=9.9 Hz, 3F), −120.16 (m, 2F), −122.42 (m, 6F), −123.16 (m, 2F), −123.82 (m, 2F), −126.57 (m, 2F).

Linear and Branched Amphiphiles.

General procedure: To a dry 100 mL flask charged with argon were added 50 mL α,α,α-trifluorotoluene (BTF) and 4.0 mmol alcohol. The mixture was cooled on ice and 5.0 mmol NaH were added. This was allowed to stir for 30 minutes before adding 2.0 mmol mPEG-OMs. The reaction was then heated to reflux and allowed to react for a 7 days. The reaction was cooled, diluted with 100 mL DCM and washed with 150 mL $NH_4Cl$ solution, 50 mL brine and dried over $MgSO_4$. The organics were then concentrated to a minimum volume and the surfactants precipitated upon addition of 500 mL cold ether. The solid was collected by vacuum filtration and then purified by reverse-phase chromatography. The product was then freeze dried from 50/50 DCM/Benzene to give a powdery solid.

M1H10-O—F3:

52% Yield, MALDI: Distribution centered on [M+Na$^+$]=1406, $^1$H NMR (400 MHz, $CDCl_3$): δ 3.90 (tt, J=13.7, 1.7 Hz, 2H), 3.84-3.81 (m, 1H), 3.75-3.71 (m, 1H), 3.68-3.61 (m, 95H), 3.60-3.54 (m, 6H), 3.44 (t, J=6.9 Hz, 2H), 3.38 (s, 3H), 1.58 (sextet, J=7.1 Hz, 4H), 1.35-1.22 (m 12H). $^{19}$F NMR (376 MHz, $CDCl_3$): δ −81.39 (3F), −121.12 (2F), −128.20 (2F); M1H10F8: 79% Yield, MALDI: Distribution centered on [M+Na$^+$]=1671, $^1$H NMR (400 MHz, $CDCl_3$): δ 3.86-3.80 (m, 1H), 3.76-3.54 (m, 98H), 3.45 (t, J=6.7 Hz, 2H), 3.38 (s, 3H), 2.05 (ttt, J=19, 8.2, 2 Hz, 2H), 1.57 (septet, J=6.7 Hz, 2H), 1.42-1.20 (m, 10H). $^{19}$F NMR (376 MHz, $CDCl_3$): δ −81.19 (3F), −114.74 (2F), −122.36 (6F), −123.16 (2F), −123.96 (2F), −126.57 (2F); All amphiphiles are at most as polydisperse as the mPEG-OH they are synthesized from (vide supra).

Miktoarm Amphiphiles.

Typical procedure: Alcohol and mPEG-OMs were dissolved in 20-75 mL BTF to achieve 20 mM concentrations. Flask flushed with Ar, NaH added (to achieve 40 mM concentration), and flask heated to reflux. After 5 days reaction was cooled to room temperature and quenched dropwise with $H_2O$. The organics were dried over $MgSO_4$. Solvents evaporated under reduced pressure, and crude polymer purified by reverse phase chromatography. Solid was lyophilized to give white, fluffy product.

M1μH10F8:

89% Yield, MALDI: Distribution centered on [M+Na$^+$]=1715, $^1$H NMR (400 MHz, $CDCl_3$): δ 4.02 (t, J=14 Hz, 2H), 3.81 (m, 1H), 3.75 (dd, J=10.4, 3.6 Hz, 2H), 3.67-3.62 (m, 80H), 3.59-3.51 (m, 7H), 3.46 (m, 1H), 3.38 (s, 3H), 1.57 (p, J=7.2 Hz, 2H), 1.26 (m, 16H), 0.88 (t, J=6.8 Hz, 3H). $^{19}$F NMR (400 MHz, $CDCl_3$): δ −81.14 (3F), −120.18 (2F), −122.36 (6F), −123.09 (2F), −123.77 (2F), −126.48 (2F). All amphiphiles are at most as polydisperse as the mPEG-OH they are synthesized from (vide supra).

Emulsion Preparation

Surfactant with or without E80 Additive Emulsion.

To a 50 mL falcon tube were added 16.82 mL normal saline, 25 mg mL$^{-1}$ surfactant and, if included, 12 mg mL$^{-1}$ Lipoid E80. This was vortexed for 1 minute and sonicated for 30 minutes with heating. The resulting solution was allowed to cool to room temperature and then 0.18 mL propofol was added and the mixture homogenized by high-speed mixing (21,000 rpm) for 1 minute. The crude emulsion was then refined by microfluidization (5,000 psi) for 1 minute. The resulting emulsion was then filtered with a 0.45 μm nylon filter and stored at 4° C.

Analysis Section No. 2

Propofol is the most common agent for induction of general anesthesia in the United States. In addition, it is commonly used for maintenance of anesthesia as well as sedation in the operating room and intensive care unit. The formulation available clinically (Diprivan®) is a lipid emulsion of 1% propofol with 10% soybean oil, 1.2% egg yolk lecithin, and 2.25% glycerol. This formulation is clinically effective but it does have several drawbacks, including the allowance of microbial growth, effects related to hyperlipidemia (elevated triglycerides and propofol infusion syndrome), and pain on injection. Although minor, anaphylaxis has also been of concern. Because of these issue, many attempts have been made to reformulate the drug. These attempts have included the addition of preservatives and anti-microbials, variations of oil and lecithin content, changes in size of triglycerides, and a host of new solvents. In this set of experiments, we studied four propofol nanoemulsions using novel surfactants, and compared their anesthetic effects to those of Diprivan® in rats. In addition, we tested whether a bolus of Intralipid® administered during the recovery phase would accelerate emergence from anesthesia.

All animal studies were approved by the University of Wisconsin Animal Care and Use Committee, Madison, Wis. Experiments to measure loss and recovery of the righting reflex were carried out in six male Sprague-Dawley rats weighing approximately 280 g. The rats were received from the supplier with a surgically-implanted jugular catheter. Five different propofol formulations were tested: 1) Diprivan®; 2) lipid-free formulation using a semifluorinated surfactant and egg lecithin designated L3; 3) lipid-free formulation using a semifluorinated surfactant designated B8; 4) lipid-free formulation using a semifluorinated surfactant and PFOB designated F8; 5) lipid-free formulation using only Lipoid E80 designated L80. For each formulation, five different bolus doses ranging from 5-15 mg/kg were administered 5 times each over 20 s using a syringe pump. In all cases, the rats received only one dose of anesthetic per day. Subsequently, the anesthetic effects of B8 and Diprivan® were tested for reversibility utilizing an Intralipid® bolus after an induction dose. Intralipid® doses from 3.75-15 ml/kg were tested in combination with 15 mg/kg of B8 or Diprivan®.

Four of the five formulations showed efficacy in causing loss of the righting reflex. The one exception was L80, which did not induce anesthesia at doses up to 15 mg/kg. The other formulations all induced LORR, all animals regained righting reflex, and no ill effects were observed during or after the anesthetic period. To compare potency of induction doses between the formulations, time to recovery of righting reflex was plotted vs log dose. For each data set, the linear regression line crossing the x-axis was considered the threshold dose for causing loss of righting reflex. There were no significant differences between the threshold doses for the four drugs: 5.2, 6.0, 5.5, and 6.8 mg/kg for Diprivan®, L3, B8, and F8 respectively. Using a similar method for evaluating the effect of Intralipid® bolus, time to recovery of righting reflex was plotted vs log dose with the slope of the linear regression line representing clearance. A 39% (p=0.014) and 51% (p=0.046) reduction in slope were seen for Diprivan® and B8, respectively.

The three lipid-free fluoropolymer-based formulations of propofol all showed similar efficacy, potency, and duration in producing and maintaining anesthesia with bolus dosing, comparable to Diprivan. Additionally, clearance of propofol from its effect site was accelerated with Intralipid® after an induction dose. These lipid free formulations have the potential to avoid complications related to microbial growth and hyperlipidemia that are seen with the currently available formulation of propofol. Further study is indicated to determine toxicity and side effect profiles of these novel surfactant formulations before they can be considered for clinical use.

Introduction

Propofol is commonly used for induction and maintenance of general anesthesia, and for sedation in the operating room and intensive care unit. Initially tested for administration in Cremophor EL, the formulation now available clinically (Diprivan®; AstraZeneca, London, United Kingdom) is a lipid-based emulsion consisting of 1% propofol together with 10% soybean oil, 1.2% egg yolk lecithin, and 2.25% glycerol. (Baker) This formulation is clinically effective but it does have several drawbacks, including emulsion instability (Park, Han), the opportunity for microbial growth (Bennett, Wachowski, Langevin), effects related to hyperlipidemia (elevated triglycerides and propofol infusion syndrome) (Wolf, Wong, Mayette, Rosen), and pain on injection. (Tan) Although rare, anaphylaxis has also been of concern. (Laxenaire, De Leon-Casasola)

Many different formulations of propofol have been studied in an attempt to remedy these issues. Preservatives and anti-microbial agents such as EDTA and sodium metabisulfite have been added. (Baker, Thompson) The oil and lecithin contents have been varied. (Song) Different sizes of triglycerides and new solvents have been tested. (Rau, Egan) Propofol's interaction with local endothelium, caused either by free propofol in the aqueous phase or by the drug being released rapidly from the oil phase, has been implicated in causing pain with injection. (Damitz1, Dubey, Ohmizo) Therefore, alternative emulsions have been developed to minimize the free concentration in an attempt to minimize this problem. (Cai, Damitz2) Prodrugs of propofol such as fospropofol are clinically available and have decreased pain on injection but have slower onset and prolonged elimination half-life. (Pergolizzi) Recently, Aquafol (Daewon Pharmaceutical Co., Ltd., Seoul, Korea), a 1% propofol microemulsion with 10% purified poloxamer 188 (PP188) and 0.7% poly-ethylene glycol 660 hydroxystearate (using no lipid), has become clinically available in some parts of the world. (Jung, Sim, Lee)

In this set of experiments, we studied in rats three propofol nanoemulsions prepared using novel semifluorinated surfactants, and compared their anesthetic effects to formulations containing only the classical surfactant Lipoid E80 and the clinically used formulation of Diprivan®. Semifluorinated-surfactant based emulsions have been studied as blood substitutes and also used for intravenous drug delivery, including intravenous delivery of the inhalational anesthetic sevoflurane. (Riess1, Riess2, Krafft, Fast) Semifluorinated surfactants were chosen for their unique architecture (lipophilic and fluorophilic blocks) and designed to eliminate the need to add soybean oil to the emulsion. The lipophilic moiety was intended to stabilize the dissolved propofol, and the fluorophilic moiety to stabilize the nanodroplet emulsion.

Propofol

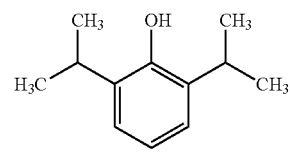

In addition to testing these emulsions for stability and efficacy, we tested whether a post-induction bolus of Intralipid® would accelerate recovery from the anesthetic effects of propofol, a highly lipid-soluble drug, as it does for the toxic effects of several lipid-soluble drugs including bupivacaine. (Weinberg/VadeBoncouer) The rationale for these studies is that the octanol:water partition coefficient (log P) of propofol is 3.79 (Babu), which makes it even more lipid soluble than bupivacaine (log P 3.41). (Hansch) If the lipid solubility of propofol causes a decreased effect site concentration with lipid infusion through partitioning, then the duration of anesthesia caused by propofol may be reduced with a lipid infusion.

Methods

Experiments were carried out in two phases. The purpose of the first phase was to demonstrate the efficacy of L3, B8, and F8 to produce anesthesia; to determine a threshold dose for causing loss of righting reflex (LORR) in the rat; and to test for adverse effects of the drugs—all in comparison to Diprivan®. The purpose of the second phase was to determine the effect of a bolus of Intralipid® on the anesthetic effects of B8 and Diprivan®.

Surfactants

The semifluorinated surfactants M1H10-O—F3 and M1μH10F8 were used in the L3 and B8 emulsions, respectively, and the classical surfactant M5diH10, and the semifluorinated surfactant M1H10F8 were used in the F8 emulsion. These emulsions were synthesized as previously reported. (Tucker)

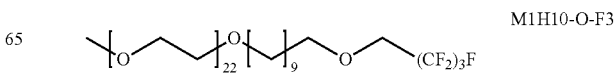

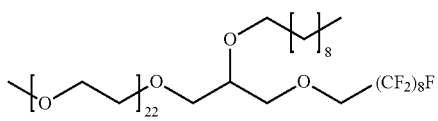
M1μH10F8

Structure of semifluorinated surfactants M1H10-O—F3 (L3) and M1μH10F8 (B8).

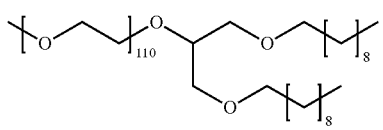
M5diH10

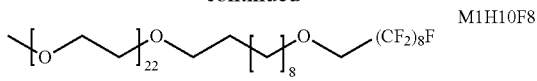
-continued
M1H10F8

Structure of classical surfactant M5diH10 and semi-fluorinated surfactant M1H10F8 (F8).

Emulsions

All emulsions were prepared by combining the surfactant, additives and propofol in water (with salt or glycerol for isotonicity). B8, L3, and M5diH10 surfactant solutions were prepared as 25 mg/mL solutions by direct dilution of lyophilized solid in sterile, normal saline solution to a total volume of 16.82 mL. The emulsion L80, containing only Lipoid E80, from Lipoid GmbH (Ludwigshafen, Germany), were prepared by dissolution of Lipoid E80 at a concentration of 12 mg/mL in 16.82 mL double-distilled water with added glycerol for isotonicity. L3 also contained 12 mg/mL Lipoid E802. The F8 surfactant solution was prepared as a 16 mg/mL solution in 13.42 mL normal saline with 3.4 mL perfluorooctyl bromide (PFOB) from Synquest Labs (Alachua, Fla.). The solutions were sonicated until completely dissolved. A 0.18 mL volume of 2,6-diisopropylphenol from Sigma Aldrich Co. (Milwaukee, Wis.) was added to the polymer solutions for a total volume of 17 mL. The high-speed homogenizer (Power Gen 500) from Fisher Scientific (Hampton, N.H.) and the microfluidizer (model 110 S) from Microfluidics Corp. (Newton, Mass.) were first cleaned with 70% and 100% ethanol, followed by 70% and 100% methanol, and finally with three rinses of Millipore water. Once prepared, each emulsion mixture was then homogenized with the high-speed homogenizer for 1 min at 21000 rpm at room temperature. The crude emulsion was then microfluidized for 1 min at 5000 psi with the cooling bath kept at 10° C. The final emulsion was then filtered with a 30 mm dia., 0.45 μm nylon filter and stored in 45 mL plastic centrifuge tubes from Corning Inc. (Corning, N.Y.) at 4° C. After preparation and filtration of the emulsions, the emulsion droplet sizes were measured by dynamic light scattering (NICOMP 380ZLS) from Particle Sizing Systems (Santa Barbara, Calif.). An aliquot of the emulsion, approximately 150 μL, was diluted in 3 mL of Millipore water to achieve an intensity factor range of 300-350. Each measurement was run for 5 minutes at room temperature and repeated in triplicate. The data were analyzed by Gaussian analysis and reported as a volume-weighted average diameter. The emulsion errors for all polymers were taken as an average of the standard deviations of each individual measurement.

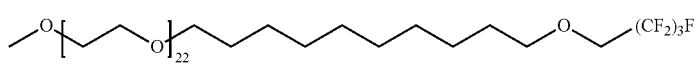
L3

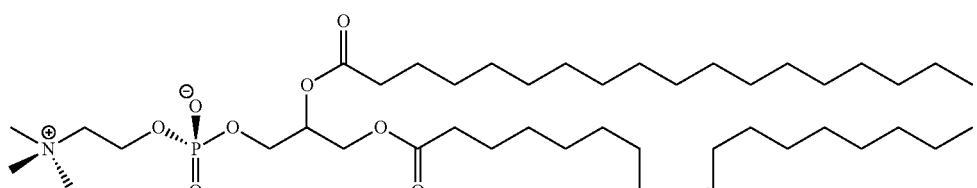
E80 (egg lecithin)

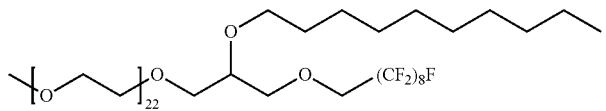
B8

Structures of L3, E80, and B8

Animal Studies

All animal studies were approved by the University of Wisconsin Animal Care and Use Committee, Madison, Wis., and were performed in accordance with the guidelines laid out in the Guide for the Care and Use of Laboratory Animals published by the National Research Council.

Phase I and 2 experiments were carried out in six male Sprague-Dawley rats (Harlan Spraque-Dawley, Inc., Indianapolis, Ind.) weighing approximately 280 g. The rats were received from the supplier with a surgically implanted jugular catheter. In all cases, the rats received only one dose of anesthetic per day.

In phase I, experiments to measure loss and recovery of righting reflex were conducted using five different propofol formulations: 1) Diprivan®; 2) L3; 3) B8; 4) F8; and 5) L80. For each of the first three formulations, five different doses (5-15 mg/kg) were administered five times each. For F8 each of the five doses was administered three times each. For L80, the highest dose (15 mg/kg) was tested five times. Since this dose did not lead to LORR, a limited number of lower doses were studied, and none led to LORR. Dosing was based on previously published data for propofol in rats. (Adam, Glen, Brammer).

The propofol emulsions were administered by first weighing the rat and then restraining it with a towel. The plug placed at the end of the catheter was then removed and replaced with a 23-gauge blunt tip needle connected to an insulin-type syringe. To remove the heparin-based fill solution and check that no blockage was obstructing the catheter, the syringe plunger was slowly withdrawn until blood filled the catheter. The 23-gauge blunt tip needle was then removed and the catheter was connected using a 23-gauge connector tip to the tubing and syringe containing the propofol emulsion to be tested. The rat was placed in a transparent cage for observation. Forty µl of the emulsion, corresponding to the volume of the catheter was injected to prime the catheter and then the administration of the emulsion was started. The emulsion injection rate was controlled through an infusion pump (11 plus; Harvard Apparatus, Holliston, Mass.). A bolus dose was delivered over 20 s regardless of the dose. LORR was evaluated by rolling the rat onto its back and observing whether the animal was able to right itself. The times to achieve and to recover from LORR were recorded. When the rat completely recovered from LORR, the catheter was flushed with 40 µl of 0.9% saline solution to remove the residual emulsion and then refilled with 40 µl of a heparin-based fill solution. The end of the catheter was sealed with a sterile plug.

In phase 2, experiments to measure the effect of an Intralipid® bolus on the anesthetic effects of Diprivan® and B8 were conducted. For both, three different doses (7.5-15 mg/kg) were administered five times each. The three doses chosen reliably caused LORR with both emulsions as determined in phase 1. In the same fashion as in phase 1, the rats were restrained and connected to the tubing and syringe containing the propofol emulsion. Procedures for bolus dose administration and determination of loss and recovery of righting reflex were carried out as in phase 1. Sixty seconds after starting the bolus propofol dose, the animals' catheters were connected to tubing and a syringe containing Intralipid® (20% lipid emulsion). A bolus of Intralipid® was then administered over 60 seconds. For the highest propofol dose administered, three different Intralipid® bolus doses were administered five times each (3.75-15 ml/kg). For the two decreased doses of propofol only the highest dose of Intralipid® was administered. Dosing was based on previously published data utilizing lipid for treatment of drug toxicity in rats. (Jamaty, Perez, Hiller, Di Gregorio, Weinberg/VadeBoncouer)

Statistics

Comparisons were made using unpaired t-tests. Differences were considered significant at a level of p<0.05.

Results

Emulsion Stability

Figure 11:
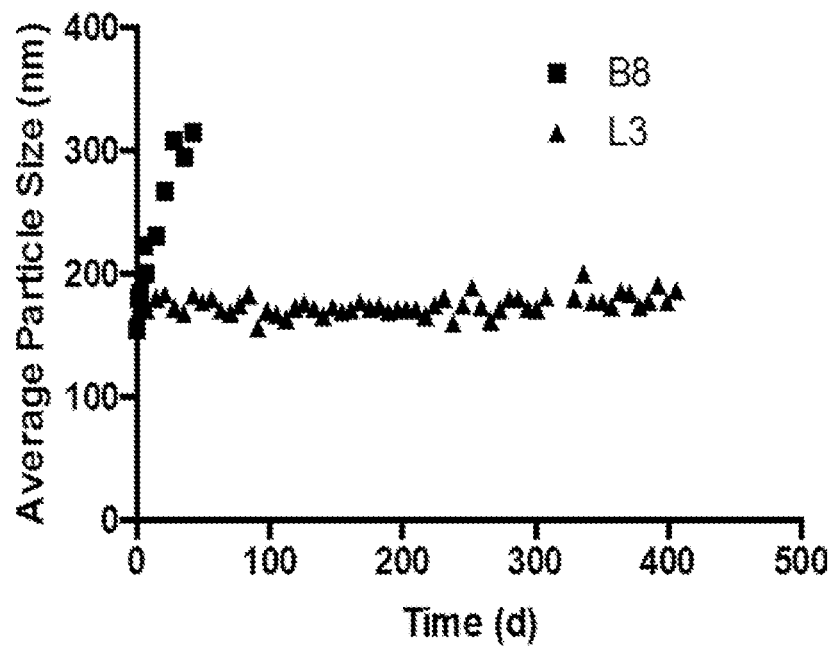
FIG. 11. provides a plot showing the average particle size (nm) for the emulsions corresponding to formulations B8 and L3 evaluated as a function of time (days).

In an effort to eliminate any added soybean oil from the developed propofol emulsions, semi-fluorinated surfactants were investigated for their ability to solubilize propofol (hydrophobic moiety) and stabilize the nanodroplet (fluorinated moiety). It was found that B8 formulation—containing only M1 pH10F8 surfactant, as shown in FIG. 11, and propofol dispersed in normal saline—formed an emulsion stable for 42 days with a growth rate of 3.60 nm/day. A similar formulation using M1H10-O—F3 failed to produce a stable emulsion. As shown in FIG. 11, the stable formulation L3 utilized M1H10-O—F3 and Lipoid E80 as equimolar co-surfactants, was stable for 406 days, with a growth rate of 0.02 nm/day.

Figure 12:
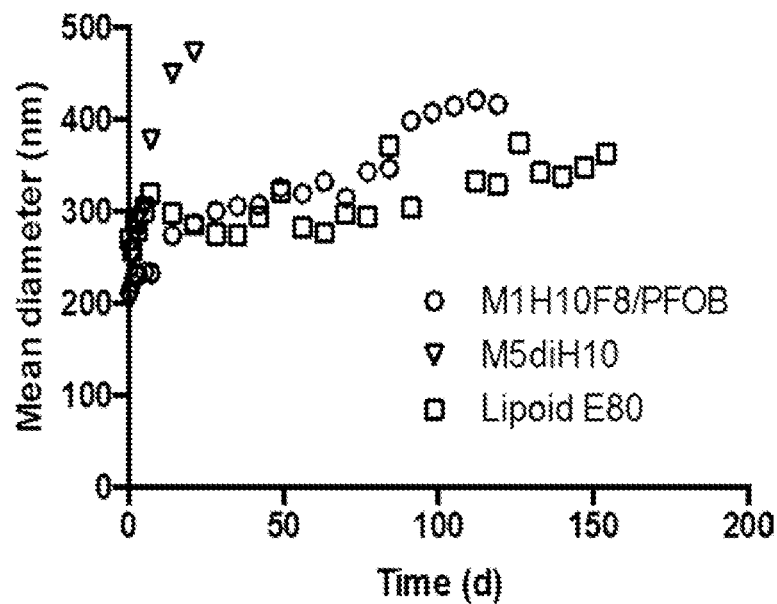
FIG. 12. provides a plot showing the average particle size (nm) for the emulsions corresponding to formulations M1H10F8/PFOB, M5diH10, and Lipoid E80 evaluated as a function of time (days).

The results of further investigations into the emulsion formulation are shown in FIG. 12. It was found that the classical (hydrophilic-lipophilic) surfactant M5diH10 did emulsify propofol and was stable for 21 days with a growth rate of 12.52 nm/day, but the emulsion rapidly grew in size. Lipoid E80—the surfactant used in Diprivan®—also formed stable emulsions, when glycerol instead of salt was used to achieve isotonicity. The emulsion was stable for 154 days with a growth rate of 0.50 nm/day. The final emulsion formulation investigated utilized a linear, semifluorinated surfactant M1H10F8, structurally similar to L3, but incorporated a fluorinated stabilizer (perfluorooctyl bromide, PFOB) instead of a phospholipid co-surfactant. This emulsion was found to be stable for 119 days with a growth rate of 1.65 nm/day.

Phase I—Emulsion Efficacy

The L80 caused only mild sedation and failed to cause LORR up to a propofol dose of 15 mg/kg.

Figure 13:
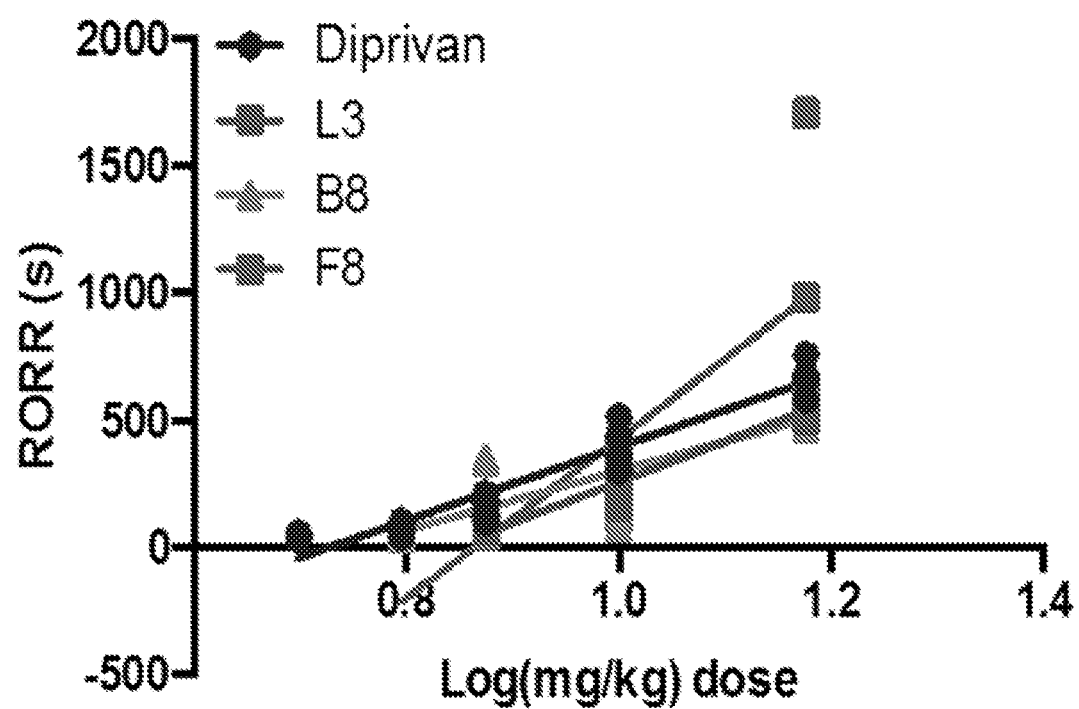
FIG. 13. provides plots of time to Time to Return of Righting Reflex (s) as a function of the logarithm of the dose (mg/kg).

The five bolus doses tested of Diprivan®, L3, B8 and F8 were 5, 6.25, 7.5, 10 and 15 mg/kg. All three formulations proved effective in causing LORR, as shown in FIG. 13. F8 proved to be effective at inducing anesthesia, but only at higher doses (compared to B8, L3 and Diprivan) and with prolonged duration at the highest, 15 mg/kg, dose.

Data are plotted as time to loss or recovery of righting reflex as a function of drug dose, expressed on a mg/kg basis for the propofol component of the nanoemulsion. The x-axis intersection is the calculated threshold dose for inducing LORR as a surrogate for unconsciousness. (Liao)

There was no significant difference between threshold doses of Diprivan® and B8. The L3 threshold dose was slightly, but significantly higher. No ill effects were seen in the rats acutely, or after >10 doses over a two week period.

Table I shows that for the three doses that reliably caused LORR, time to recovery of righting reflex was significantly longer for Diprivan® compared to L3 and B8.

TABLE I

Duration of Anesthesia versus Dose for Diprivan, L3, and B8
Duration of anesthesia (s)

| | 7.5 mg/kg | 10 mg/kg | 15 mg/kg |
| --- | --- | --- | --- |
| Diprivan ® | 157.60 ± 43.59 | 342.83 ± 155.95 | 668.8 ± 60.35 |
| L3 | 65.33 ± 33.97 | 220.20 ± 49.30 | 554.60 ± 45.52 |
| B8 | 189.67 ± 168.94 | 190.6 ± 104.11 | 548.60 ± 63.03 |

For 7.5 mg/kg doses, duration of anesthesia of L3 was significantly shorter (p=0.005) than Diprivan®; B8 was not significantly different than Diprivan® or L3. For 10 mg/kg doses, duration of anesthesia of L3 and B8 were significantly shorter (p=0.0034 and p=0.0067, respectively) than Diprivan®; B8 and L3 were not significantly different from one another. For 15 mg/kg doses, duration of anesthesia of L3 and B8 were significantly shorter (p=0.0108 and p=0.0151, respectively) than Diprivan®; B8 and L3 were not significantly different from one another.

Phase 2—Intralipid® Studies

The three bolus doses tested of Diprivan® and B8 were 7.5, 10, and 15 mg/kg.

Figure 14:
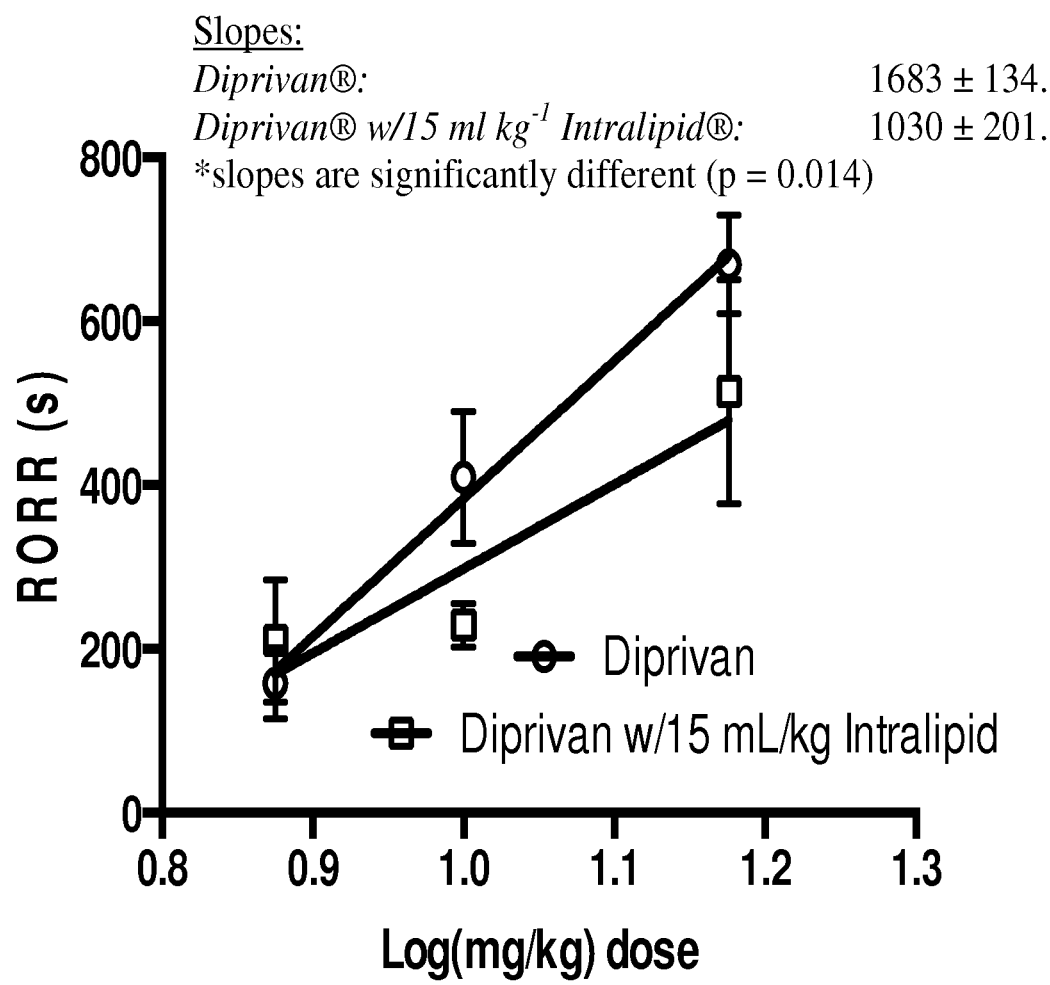
FIG. 14. provides plots of time to Time to Return of Righting Reflex (s) as a function of the logarithm of the dose (mg/kg).

FIG. 14 provides a plot for Diprivan® with 15 ml kg$^{-1}$ Intralipid®. The data are plotted as time to recovery of righting reflex as a function of drug dose, expressed on a mg/kg basis for the propofol component of the nanoemulsion. Using the slope of the trendline to represent rate of clearance, the lower the slope the more rapid the clearance of propofol from its effect site (faster recovery of righting reflex for a given dose).

The slope of the line using Diprivan® followed by Intralipid® is 39% less than the slope of the line using Diprivan® alone. This is a significant difference (p=0.014).

There was greater reduction in duration of anesthesia for higher doses (10, 15 mg/kg) and virtually no change for the 7.5 mg/kg dose.

Figure 15:
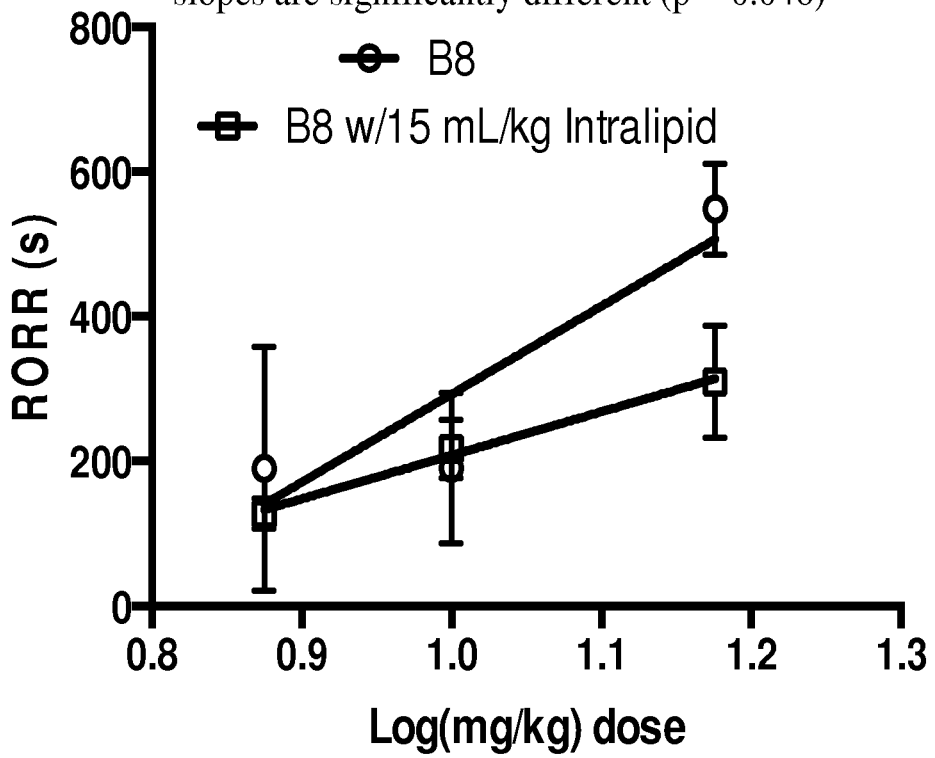
FIG. 15. provides plots of time to Time to Return of Righting Reflex (s) as a function of the logarithm of the dose (mg/kg).

FIG. 15 provides a plot for B8 with 15 ml kg$^{-1}$ Intralipid®. The data are plotted as time to recovery of righting reflex as a function of drug dose, expressed on a mg/kg basis for the propofol component of the nanoemulsion.

Again, a reduction (51%) in the slope of the trend line was seen using B8 with Intralipid®. This is significantly different (p=0.046). However, most of this reduction was due to the 15 mg/kg dose with little, if any, reduction for the 7.5 and 10 mg/kg doses.

Figure 16:
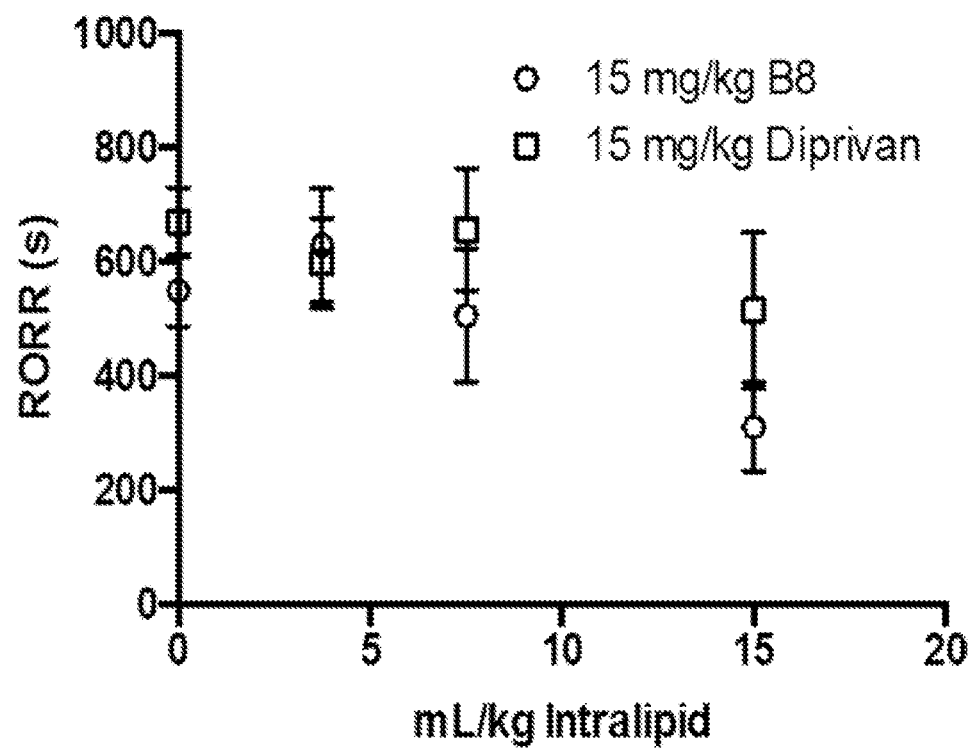
FIG. 16. provides plots of time to Time to Return of Righting Reflex (s) vs Intralipid® dose (mL/kg).

FIG. 16 provides a plot for B8 and Diprivan® with Intralipid®. The data are plotted as time to return of righting reflex vs Intralipid® dose. Large doses (15 mg/kg) of B8 and Diprivan® were administered in combination with decreasing doses of Intralipid® (15, 7.5, and 3.75 ml/kg). Error bars are added.

The 15 ml/kg dose of Intralipid® caused a significant reduction in duration of anesthesia for B8 (p=0.0008), and a noticeable but not significant decrease for Diprivan® (p=0.0632). The smaller doses (3.75 and 7.5 ml/kg) of Intralipid® cause little, if any, reduction compared to 15 mg/kg doses without the addition of Intralipid®.

Discussion

These novel fluoropolymer emulsions of propofol, L3, B8, and F8 were able to reliably induce anesthesia in rats. There were no ill effects either acutely or after more than 10 administrations over a 2-3 week period. The threshold dose of the emulsion containing only fluoropolymer and propofol, B8, was not significantly different than that of Diprivan® in rats; the threshold dose of L3 and F8 were only slightly higher. In regards to duration of anesthesia after a bolus dose, B8 and L3 were not significantly different across all doses. For higher doses (10 and 15 mg/kg) B8 and L3 produce a significantly shorter duration of anesthesia than Diprivan®, and F8 longer. This may be due to decreased bioavailability or slower release of propofol in the B8 and L3 emulsions, and especially in F8, compared to Diprivan®.

Interestingly, the formulation containing only propofol and Lipoid E80 did not cause LORR even at high doses. Additionally, the L3 emulsion, which contained Lipoid E80, required a higher threshold dose to cause LORR than B8, which did not contain the surfactant. If Lipoid E80 is a factor in the bioavailability of propofol from the emulsions, it may be possible to vary its concentration to affect release of the drug. This could have implications for pain on injection as well as hemodynamic instability after bolus dosing.

These 3 formulations of propofol all showed similar efficacy, potency, and duration in producing and maintaining anesthesia with bolus dosing. Additionally, clearance of propofol from its effect site can be accelerated with Intralipid® after an induction dose. This effect was observed even with the lipid-based formulation (Diprivan®), but was stronger for the lipid-free formulation B8. The effect was most significant when a high dose of drug (15 mg/kg) was followed by a high volume of lipid (15 ml/kg).

Several mechanisms have been proposed for lipid rescue in toxicity from bupivacaine as well as other drugs. The most commonly cited is via "partitioning" in which the lipid acts as an intravascular "sink," causing decreased concentrations of drug at the effect site. A second proposed mechanism is the accelerated shunting of the drug to its site of metabolism, which is typically the liver for lipid-soluble drugs. (Weinberg, Weinberg/VadeBoncouer, Weinberg/Ripper) In either case, there is increased clearance of the drug from the effect site, which in the case of propofol is GABAa receptors in the CNS. We see this in the decreased slope of the linear regression lines when propofol administration is followed by Intralipid® bolus. Partitioning has been proposed as a mechanism for several lipid soluble drugs (local anesthetics, calcium channel blockers, beta blockers, etc.) whose toxicity has been treated with lipid infusion. (Jamaty, Perez) This could partially explain our results in that propofol, log P (octanol:water partition coefficient) 3.79 (Babu), is more lipid soluble than bupivacaine, which has a log P of 3.41. (Hansch)

It would follow then that a high lipid dose would shorten duration of anesthesia more than a lower dose, but we saw a lack of effect with 7.5 and 3.75 ml/kg doses of Intralipid®. There is some evidence that in bupivacaine toxicity, lipid works to reverse inhibition of fatty acid metabolism in cardiac muscle. (Weinberg) It may be possible that Intralipid® interferes with propofol binding to the GABAa receptor, and that there is a threshold concentration required to see this effect, which the 7.5 and 3.75 ml/kg doses are not large enough to reach.

The 15 ml/kg dose of Intralipid® that was found to be effective in this study is relatively large. However, it is possible that lower volumes would be effective in a human as compared to the rat. Induction of anesthesia in humans typically requires 1-2 mg/kg, but in rats that dose is 5-10 times higher. A similar reduction in Intralipid® dose to 1.5-3 ml/kg or less may have particular clinically utility.

REFERENCES

Baker M T, Naguib M: Propofol the challenges of formulation. Anesthesiology 2005; 103:860-76

Park J W, Park E S, Chi S C, Kil H Y, Lee K H: The effect of lidocaine on the globule size distribution of propofol emulsions. Anesth Analg 2003; 97:769-71

Bennett S N, McNeil M M, Bland L A, Arduino M J, Villarino M E, Perrotta D M, Burwen D R, Welbel S F, Pegues D A, stroud I, Zeitz P S, Jarvis W R: Postoperative infections traced to contamination of an intravenous anesthetic, propofol. N Engl J Med 1995; 333:147-54

Wachowski I, Jolly D T, Hrazdil J, Galbraith J C, Greacen M, Clanachan A S: The growth of microorganisms in propofol and mixtures of propofol and lidocaine Anesth Analg 1999; 88:209-12

Langevin P B, Gravenstein N, Doyle T J, Roberts S A, Skinner S, Langevin S O, Gulig P A: Growth of *Staphylococcus aureus* in Diprivan and Intralipid: Implications on the pathogenesis of infections. Anesthesiology 1999; 91:1394-400

Wolf A, Weir P, Segar P, Stone J, Shield J: Impaired fatty acid oxidation in propofol infusion syndrome. Lancet 2001; 357:606-7

Wong J M: Propofol infusion syndrome. Am J Ther 2010; 17:487-91

Mayette M, Gonda J, Hsu J L, Mihm F G: Propofol infusion syndrome resuscitation with extracorporeal life support: a case report and review of the literature. Ann Intensive Care 2013; 3:32

Rosen D J, Nicoara A, Koshy N, Wedderburn R V: Too much of a good thing? Tracing the history of the propofol infusion syndrome. J Trauma 2007; 63:443-7

Tan C H Onsiong M K: Pain on injection of propofol. Anaesthesia 1998; 53:468-76

Laxenaire M C, Gueant J L, Bermejo E, Mouton C: Anaphylactic shock due to propofol. Lancet 1988; 2:739-40

De Leon-Casasola O A, Weiss A, Lema M J: Anaphylaxis due to propofol. Anesthesiology 1992; 77:384-6

Han J, Davis S S, Washington C: Physical properties and stability of two emulsion formulations of propofol. Int J Pharm 2001; 215: 207-20

Thompson K A, Goodale D B: The recent development of propofol (DIPRIVAN). Intens Care Med 2000; 26 (Suppl. 4): S400L 404

Song D1, Hamza M, White P F, Klein K, Recart A, Khodaparast O: The pharmacodynamic effects of a lower-lipid emulsion of propofol: a comparison with the standard propofolemulsion. Anesth Analg 2004; 98:687-91

Rau J, Roizen M F, Doenicke A W, O'Connor M F, Strohschneider U: Propofol in an emulsion of long- and medium chain triglycerides: the effect on pain. Anesth Analg 2001; 93:382-4

Egan T D, Kern S E, Johnson K B, Pace N L: The pharmacokinetics and pharmacodynamics of propofol in a modified cyclodextrin formulation (Captisol) versus propofol in a lipid formulation (Diprivan): an electroencephalographic and hemodynamic study in a porcine model. Anesth Analg 2003; 97:72-9

Damitz R, Chauhan A: Rapid dissolution of propofol emulsions under sink conditions. Int J Pharm 2015; 481:47-55

Dubey P K, Kumar A: Pain on injection of lipid-free propofol and propofol emulsion containing medium-chain triglyceride: A comparative study. Anesth Analg 2005; 101:1060-2

Ohmizo H, Obara S, Iwama H: Mechanism of injection pain with long and long-medium chain triglyceride emulsive propofol. Can J Anaesth 2005; 52: 595-9

Cai W, Deng W, Yang H, Chen X, Jin F: A propofol microemulsion with low free propofol in the aqueous phase: formulation, physicochemical characterization, stability and pharmacokinetics. Int J Pharm 2012; 436: 536-44

Damitz R, Chauhan A: Kinetically stable propofol emulsions with reduced free drug concentration for intravenous delivery. Int J Pharm 2015; 486:232-41

Pergolizzi Jr J V, Can, T J, Plavin S, Labhsetwar S, Taylor R: Perspectives on the role of fospropofol in the monitored anesthesia care setting. Anesthesiol Res Pract 2011; 458920

Jung J A, Choi B M, Cho S H, Choe S M, Ghim J L, Lee H M, Roh Y J, Noh G J: Effectiveness, safety, and pharmacokinetic and pharmacodynamics characteristics of microemulsion propofol in patients undergoing elective surgery under total intravenous anaesthesia. Br J Anaesth 2010; 104:563-76

Sim, J Y, Lee S H, Park D Y, Jung J A, Ki K H, Lee D H, Noh G J: Pain on injection with microemulsion propofol. Br J Clin Pharmacol 2009; 67: 316-25

Lee E, Lee S, Park D, Ki K, Lee E, Lee D, Noh G: Physicochemical properties, pharmacokinetics and pharmacodynamics of a reformulated microemulsion propofol in rats. Anesthesiology 2008; 109:436-47

Riess J G. Oxygen carriers ("blood substitutes")-raison d'etre, chemistry, and some physiology. Chem Rev 2001; 101:2797-920

Riess J G. Highly fluorinated systems for oxygen transport, diagnosis and drug delivery. Colloids Surf A 1994; 84:33-48

Krafft M P. Fluorocarbons and fluorinated amphiphiles in drug delivery and biomedical research. Adv Drug Deliv Rev 2001; 47:209-28

Fast J P, Perkins M G, Pearce R A, Mecozzi S: Fluoropolymer-based emulsions for the intravenous delivery of sevoflurane. Anesthesiology 2008; 109:651-6

Weinberg G L, VadeBoncouer T, Ramaraju G A, Garcia-Amaro M F, Cwik M J: Pretreatment or resuscitation with a lipid infusion shifts the dose-response to bupivacaine-induced asystole in rats. Anesthesiology 1998; 88:1071-5

Babu M K, Godiwala T N: Toward the development of an injectable dosage form of propofol: preparation and evaluation of propofol-sulfobutyl ether 7-beta-cyclodextrin complex. Pharm Dev Technol 2004; 9: 265-75

Hansch, C., Leo, A., D. Hoekman. Exploring QSAR—Hydrophobic, Electronic, and Steric Constants. Washington, D.C.: American Chemical Society 1995., p. 159

Tucker, W. B.; McCoy, A. M.; Fix, S. M; Stagg, M. F.; Murphy, M. M.; Mecozzi, S. Synthesis, physicochemical characterization, and self-assembly of linear, dibranched and miktoarm semifluorinated triphilic polymers. J. Polym. Sci. A: Polym. Chem. 2014, 52, 3324-3336.

Adam H K, Glen J B, Hoyle P A: Pharmacokinetics in laboratory animals of ICI 35 868, a new i.v. anaesthetic agent. Br J Anaesth 1980; 52:743-6

Glen J B, Hunter S C: Pharmacology of an emulsion formulation of ICI 35 868. Br J Anaesth 1984; 56:617-26

Brammer A, West C D, Allen S L: A comparison of propofol with other injectable anaesthetics in a rat model for measuring cardiovascular parameters. Lab Anim 1993; 27:250-7

Jamaty C, Bailey B, Larocque A, Notebaert E, Sanogo K: Lipid emulsions in the treatment of acute poisoning: a systematic review of human and animal studies. Clin Toxicol (Phila) 2010; 48:1-27

Perez E, Bania T C, Medlej K, Chu J: Determining the optimal dose of intravenous fat emulsion for the treatment of severe verapamil toxicity in a rodent model. Acad Emerg Med 2008; 15:1284-9

Hiller D B, Di Gregorio G, Kelly K, Ripper R, Edelman L, Boumendjel R, Drasner K, Weinberg G L: Safety of high volume lipid emulsion infusion a first approximation of LD50 in rats. Reg Anesth Pain Med 2010; 35:140-4

Di Gregorio G, Schwartz D, Ripper R, Kelly K, Feinstein D L, Minshall R D, Massad M, Ori C, Weinberg G L; Lipid emulsion in superior to vasopressin in a rodent model of resuscitation from toxin-induced cardiac arrest. Crit Care Med 2009; 37:993-999

Liao M, Sonner J M, Husain S S, Miller K W, Jurd R, Rudolph U, Eger E I: R (+) etomidate and the photoactivable R (+) azietomidate have comparable anesthetic activity in wild-type mice and comparably decreased activity in mice with a N265M point mutation in the gamma-aminobutyric acid receptor B3 subunit. Anesth Analg 2005; 101:131-5

Weinberg G L: Lipid emulsion infusion resuscitation for local anesthetic and other drug overdose. Anesthesiology 2012; 117:180-7

Weinberg G, Ripper R, Feinstein D L, Hoffman W: Lipid emulsion infusion rescues dogs from bupivacaine-induced cardiac toxicity. Reg Anesth Pain Med 2003; 38:198-202

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. An emulsion for delivery of a therapeutic agent, said emulsion comprising:
   an aqueous solution;
   semi-fluorinated block copolymers; wherein each of said semi-fluorinated block copolymers independently comprises a hydrophilic block, a hydrophobic block and a fluorophilic block; wherein said hydrophobic block of each of said semi-fluorinated block copolymers is provided between said fluorophilic block and said hydrophilic block; wherein each of said semi-fluorinated block copolymers has a branched structure wherein said hydrophilic block comprises a first branch, said hydrophobic block comprises a second branch and said fluorophilic block comprises a third branch;

said therapeutic agent comprising a hydrophobic compound; and a phospholipid surfactant;

said emulsion comprising a continuous phase and a dispersed phase, wherein said continuous phase comprises said aqueous solution and said dispersed phase comprises said semi-fluorinated block copolymers, said therapeutic agent and said phospholipid surfactant;

wherein each of said semi-fluorinated block copolymers independently has the formula (FX9A) or (FX9B):

$$H_3C \left( O \diagdown \right)_q OCH_2 - \underset{H}{\overset{O-(CH_2)_o-H}{C}} - OCH_2 - (CF_2)_p - F \quad \text{(FX9A)}$$

or $$H_3C \left( O \diagdown \right)_q OCH_2 - \underset{H}{\overset{O-(CH_2)_o-H}{C}} - CH_2 - (CF_2)_p - F; \quad \text{(FX9B)}$$

wherein q is an integer selected from the range of 10 to 300, o is an integer selected from the range of 5 to 20, and p is an integer selected from the range of 3 to 15.

2. An emulsion for delivery of a therapeutic agent, said emulsion comprising:

an aqueous solution;

semi-fluorinated block copolymers; wherein each of said semi-fluorinated block copolymers independently comprises a hydrophilic block, a hydrophobic block and a fluorophilic block; wherein each of said semi-fluorinated block copolymers has a branched structure wherein said hydrophilic block comprises a first branch, said hydrophobic block comprises a second branch and said fluorophilic block comprises a third branch; and said therapeutic agent comprising a hydrophobic compound;

said emulsion comprising a continuous phase and a dispersed phase, wherein said continuous phase comprises said aqueous solution and said dispersed phase comprises said semi-fluorinated block copolymers and said therapeutic agent;

wherein each of said semi-fluorinated block copolymers independently has the formula (FX9A) or (FX9B):

$$H_3C \left( O \diagdown \right)_q OCH_2 - \underset{H}{\overset{O-(CH_2)_o-H}{C}} - OCH_2 - (CF_2)_p - F \quad \text{(FX9A)}$$

or $$H_3C \left( O \diagdown \right)_q OCH_2 - \underset{H}{\overset{O-(CH_2)_o-H}{C}} - CH_2 - (CF_2)_p - F; \quad \text{(FX9B)}$$

wherein q is an integer selected from the range of 10 to 300, o is an integer selected from the range of 5 to 20, and p is an integer selected from the range of 3 to 15.

3. The emulsion of claim 2, wherein each of said fluorophilic blocks of said semi-fluorinated block copolymers is independently a fluorocarbon moiety having between 3 to 31 carbon fluorine bonds.

4. The emulsion of claim 2, wherein each of said hydrophilic blocks of said semi-fluorinated block copolymers is independently selected from the group consisting of a polyoxygenated polymer block, a polysaccharide block, a chitosan derivative block, and a poly(ethylene glycol) block.

5. The emulsion of claim 2, wherein each of said hydrophobic blocks of said semi-fluorinated block copolymers is independently selected from the group consisting of a $C_5$-$C_{20}$ alkylene group, a poly (ε-caprolactone) block, a poly(lactic acid) block; a poly(propylene glycol) block; a poly(amino acid) block; a poly(ester) block and poly(lactic-co-glycolic acid).

6. The emulsion of claim 2, wherein each of said semi-fluorinated block copolymers independently has the formula (FX10):

$$H_3C \left( O \diagdown \right)_{22} OCH_2 - \underset{H}{\overset{O-(CH_2)_{10}-H}{C}} - OCH_2 - (CF_2)_8 - F. \quad \text{(FX10)}$$

7. The emulsion of claim 1, wherein said phospholipid surfactant has the formula (FX11):

(FX11)

wherein each of $R^5$ and $R^6$ is independently hydrogen, $C_5$-$C_{20}$ alkyl, $C_5$-$C_{20}$ cycloalkyl, $C_5$-$C_{30}$ aryl, $C_5$-$C_{30}$ heteroaryl, $C_5$-$C_{20}$ acyl, $C_5$-$C_{20}$ alkenyl, $C_5$-$C_{20}$ cycloalkenyl, $C_5$-$C_{20}$ alkynyl, or $C_5$-$C_{20}$ alkylaryl.

8. The emulsion of claim 2, wherein said hydrophobic compound is characterized by a solubility in water of equal to or less than 0.7 mM.

9. The emulsion of claim 2, wherein said hydrophobic compound is an anesthetic drug.

10. The emulsion of claim 9, wherein said anesthetic drug is propofol or alfaxalone.

11. The emulsion of claim 1, wherein the hydrophobic compound has a concentration of 0.2 to 50 mg mL$^{-1}$, the phospholipid surfactant has a concentration of 10 to 20 mg mL$^{-1}$; and wherein the semi-fluorinated block copolymers have a concentration selected from the range of 10 to 50 mg mL$^{-1}$.

12. The emulsion of claim 2, wherein the hydrophobic compound has a concentration of 0.2 to 50 mg mL$^{-1}$; and wherein the semi-fluorinated block copolymers have a concentration selected from the range of 10 to 50 mg mL$^{-1}$.

13. The emulsion of claim 2, wherein said dispersed phase comprises a plurality of droplets dispersed in said continuous phase.

14. The emulsion of claim 13, wherein said droplets have an average diameter less than or equal to 400 nanometers.

15. The emulsion of claim 13, wherein said droplets do not undergo an appreciable change in size over a period of 1 day to 4 weeks.

16. The emulsion of claim 13, wherein said droplets have a hydrophilic exterior shell comprising said hydrophilic blocks of said semi-fluorinated block copolymers; an hydrophobic intermediate shell comprising said hydrophobic blocks of said semi-fluorinated block copolymers; and a fluorophilic core.

17. The emulsion of claim 2, further comprising a perhalogenated fluorous compound, wherein said perhalogenated fluorous compound is a substituted or unsubstituted fluorocarbon having a length of 4 to 20 carbons.

18. The emulsion of claim 17, wherein said perhalogenated fluorous compound is selected from the group consisting of perfluorooctyl bromide, perfluorononyl bromide, perfluorodecyl bromide, perfluorodecalin, perfluorodichlorooctane, bis-perfluorobutyl ethylene and perfluoro(methyldecalin).

19. A method of delivering a therapeutic agent to a subject in need thereof, said method comprising the steps of:

providing the emulsion of claim 2; and administering said emulsion to said subject, wherein said therapeutic agent is released from said emulsion, thereby delivering said therapeutic agent to said subject in need thereof.

20. The method of claim 19, wherein said hydrophobic compound is an anesthetic drug.

21. The method of claim 19, wherein said hydrophobic compound is propofol or alfaxalone.

22. The method of claim 19, wherein said step of administering said emulsion provides for controlled release of said hydrophobic compound from said emulsion.

23. The method of claim 19, wherein said step of administering said emulsion is carried out via intravenous injection.

24. The method of claim 19, wherein a volume of said emulsion less than or equal to 500 mL is administered to said subject.

25. The method of claim 19, wherein said emulsion is delivered to said subject at a rate less than or equal to 100 mL per minute.

* * * * *